(12) United States Patent
Look et al.

(10) Patent No.: US 6,648,026 B2
(45) Date of Patent: Nov. 18, 2003

(54) MULTI-COMPOSITION STICK PRODUCT AND A PROCESS AND SYSTEM FOR MANUFACTURING THE SAME

(75) Inventors: Jee Loon Look, York, PA (US); Paul Joseph Cooper, Chesterfield, VA (US); Khawla Abdullah Abu-Izza, Westchester, PA (US); Joyce H. Wilson, Richmond, VA (US); Krishna P. Raman, Glen Allen, VA (US); Vincent Hon-Kin Li, Mechanicsville, VA (US)

(73) Assignee: Wyeth, Madison, NJ (US)

( * ) Notice: Subject to any disclaimer, the term of this patent is extended or adjusted under 35 U.S.C. 154(b) by 0 days.

(21) Appl. No.: 09/871,155

(22) Filed: May 31, 2001

(65) Prior Publication Data

US 2002/0041788 A1 Apr. 11, 2002

Related U.S. Application Data

(63) Continuation-in-part of application No. 09/584,640, filed on May 31, 2000.

(51) Int. Cl.[7] .................................................. B65B 1/04
(52) U.S. Cl. ............................ 141/9; 141/100; 141/104
(58) Field of Search .......................... 141/9, 218, 100, 141/374, 234, 236, 99, 104, 113; 401/68

(56) References Cited

U.S. PATENT DOCUMENTS

| 2,174,779 | A | * | 10/1939 | Delorme | |
|---|---|---|---|---|---|
| 2,876,161 | A | * | 3/1959 | Gieschi | |
| 3,192,933 | A | | 7/1965 | Prince | 132/79 |
| 3,881,529 | A | * | 5/1975 | Mannara | 141/100 |
| 4,120,948 | A | | 10/1978 | Shelton | |
| 4,291,018 | A | | 9/1981 | Oeda et al. | 424/64 |
| 4,364,486 | A | | 12/1982 | Korte et al. | 215/296 |
| 4,393,643 | A | * | 7/1983 | Fryar et al. | |
| 4,602,886 | A | | 7/1986 | Smit | 401/35 |
| 4,743,443 | A | | 5/1988 | Pisani et al. | 424/63 |
| 4,786,449 | A | | 11/1988 | Smit | 264/73 |
| 4,996,044 | A | | 2/1991 | Mercado et al. | 424/64 |
| 5,089,256 | A | | 2/1992 | Scheller et al. | 424/63 |
| 5,371,131 | A | | 12/1994 | Gierenz et al. | 524/394 |
| 5,433,775 | A | | 7/1995 | Gardenier et al. | 106/211 |
| 5,503,825 | A | | 4/1996 | Lane | 424/64 |
| 5,780,018 | A | * | 7/1998 | Collins et al. | |
| 5,948,394 | A | | 9/1999 | Walling et al. | 424/64 |
| 5,965,657 | A | | 10/1999 | Voegtli et al. | 524/487 |
| 6,050,540 | A | * | 4/2000 | O'Reilly | |

FOREIGN PATENT DOCUMENTS

| CA | 2309334 | | 10/1998 |
|---|---|---|---|
| DE | 3403753 A1 | * | 11/1984 |
| DE | 19732593 A1 | * | 7/1999 |
| GB | 2297710 A | * | 8/1996 |
| JP | 61-112008 A | * | 5/1986 |
| JP | 2-172904 A | * | 4/1990 |

* cited by examiner

Primary Examiner—Gregory Huson
Assistant Examiner—Khoa Huynh
(74) Attorney, Agent, or Firm—Darby & Darby

(57) ABSTRACT

A multi-composition stick product, such as a lip balm, sun screen, deodorant, or glue stick. The multi-composition stick product including a stick composition molded in the container so as to contact the walls thereof and be advanceable or ejected therefrom. The stick composition includes a first composition and a second composition. The first and second compositions differ in at least one component, such as a medicament, colorant, fragrance, flavorant, sunscreen, preservative, conditioner, moisturizer, emollient, or surfactant. Furthermore the first and second compositions are arranged in a predetermined non-random pattern that is reproducible. Also described is the method and apparatus for manufacturing the multi-composition stick product.

19 Claims, 17 Drawing Sheets

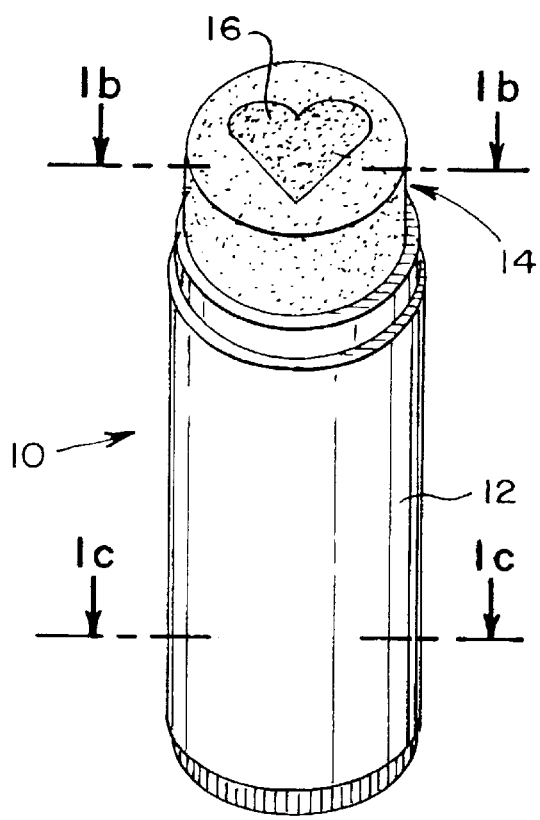
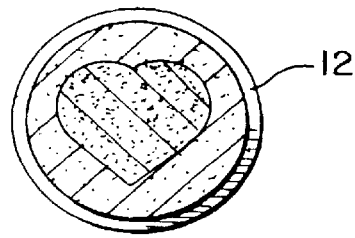
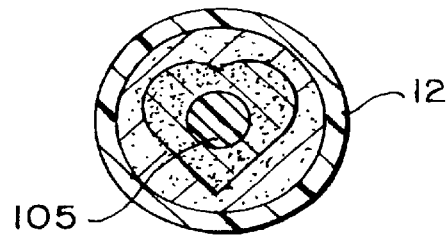
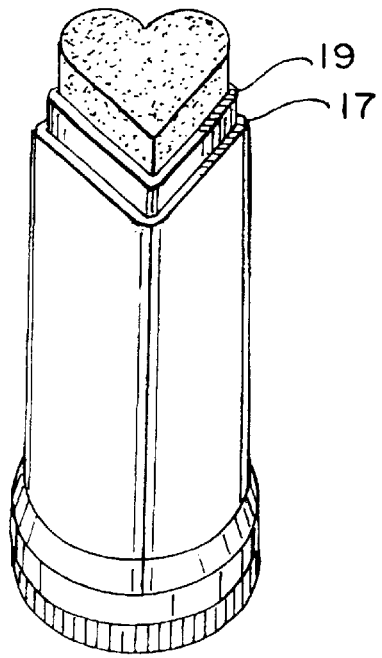
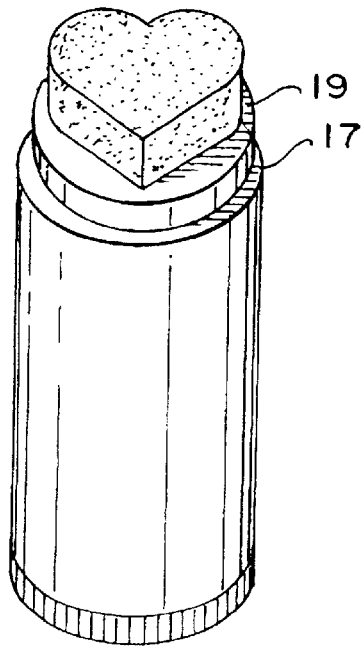

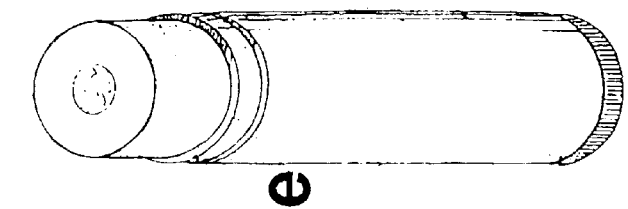
FIG. 2f
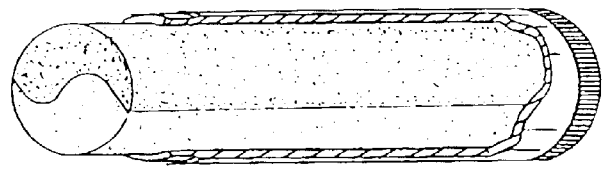
FIG. 2e
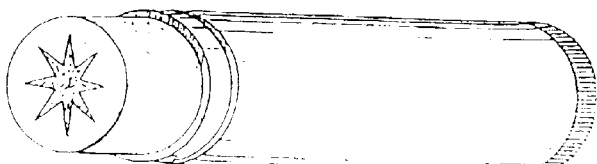
FIG. 2d
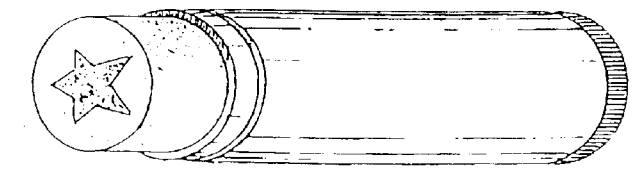
FIG. 2c
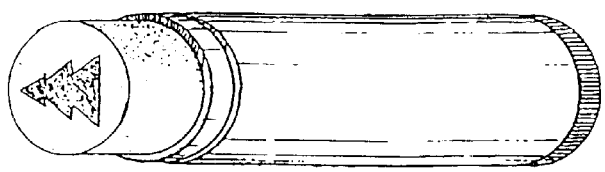
FIG. 2b
FIG. 2a

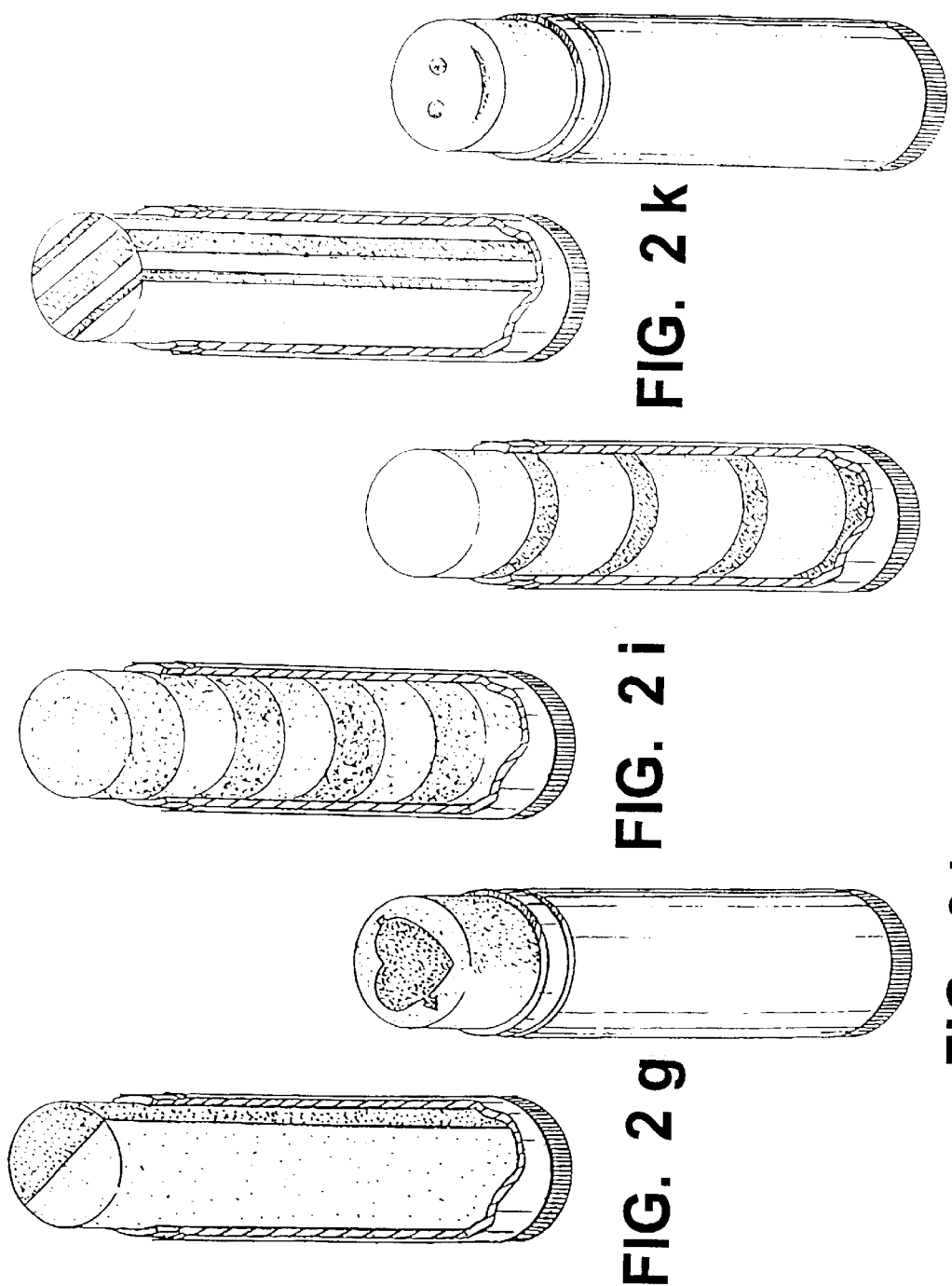

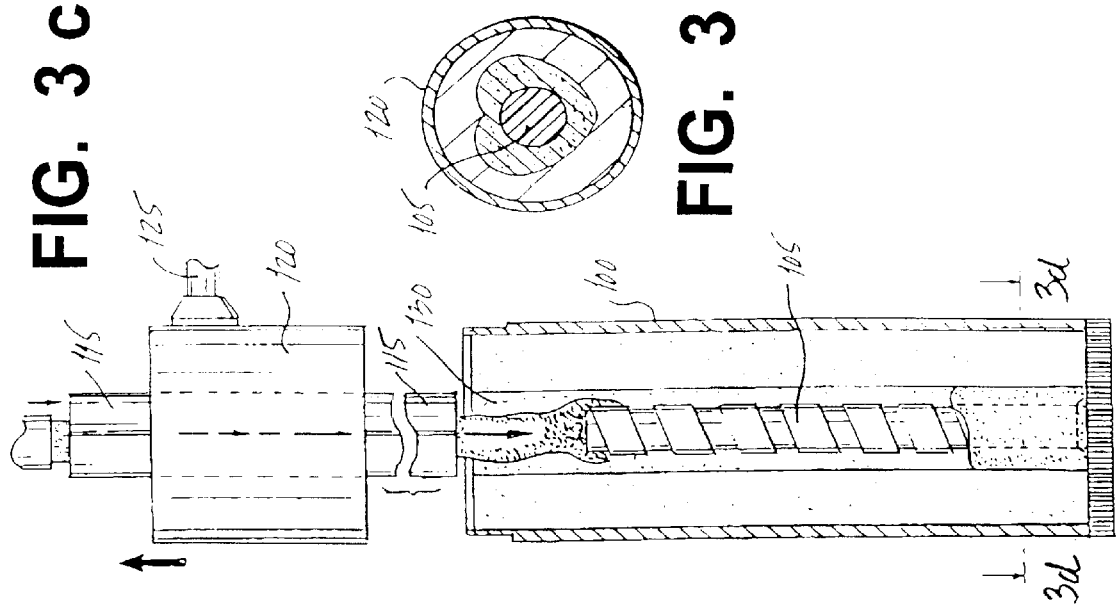
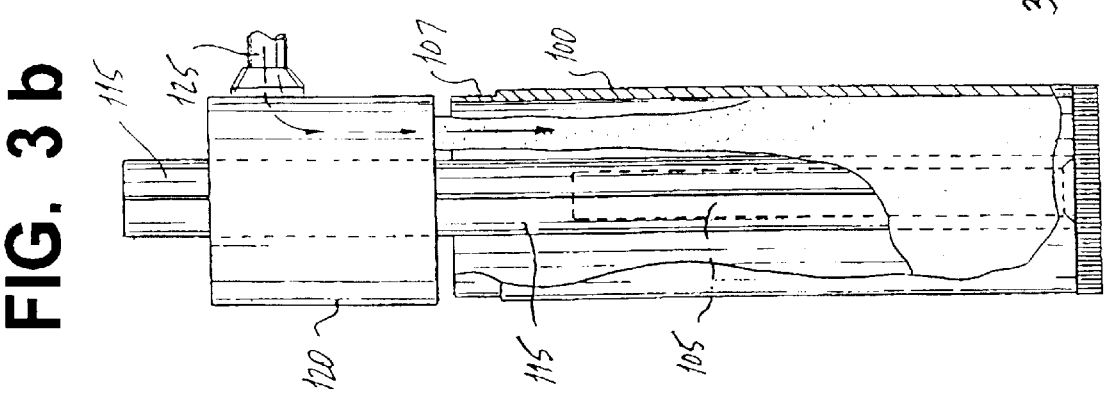
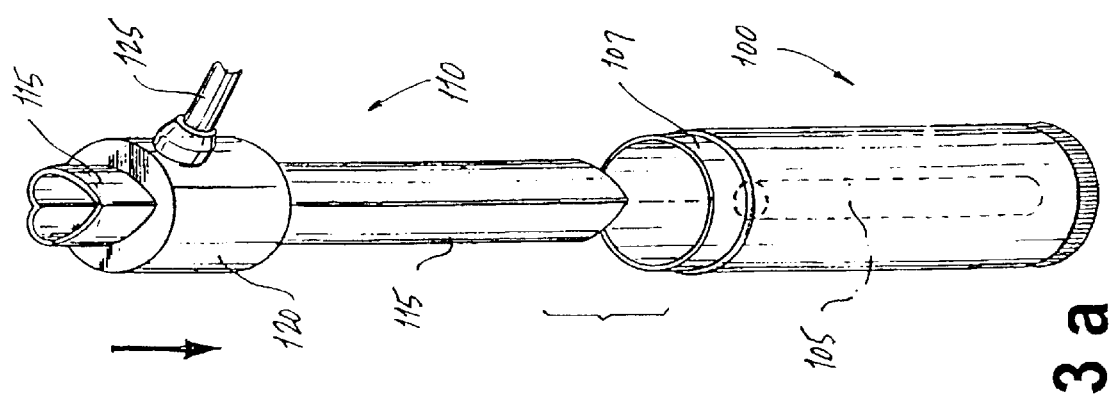

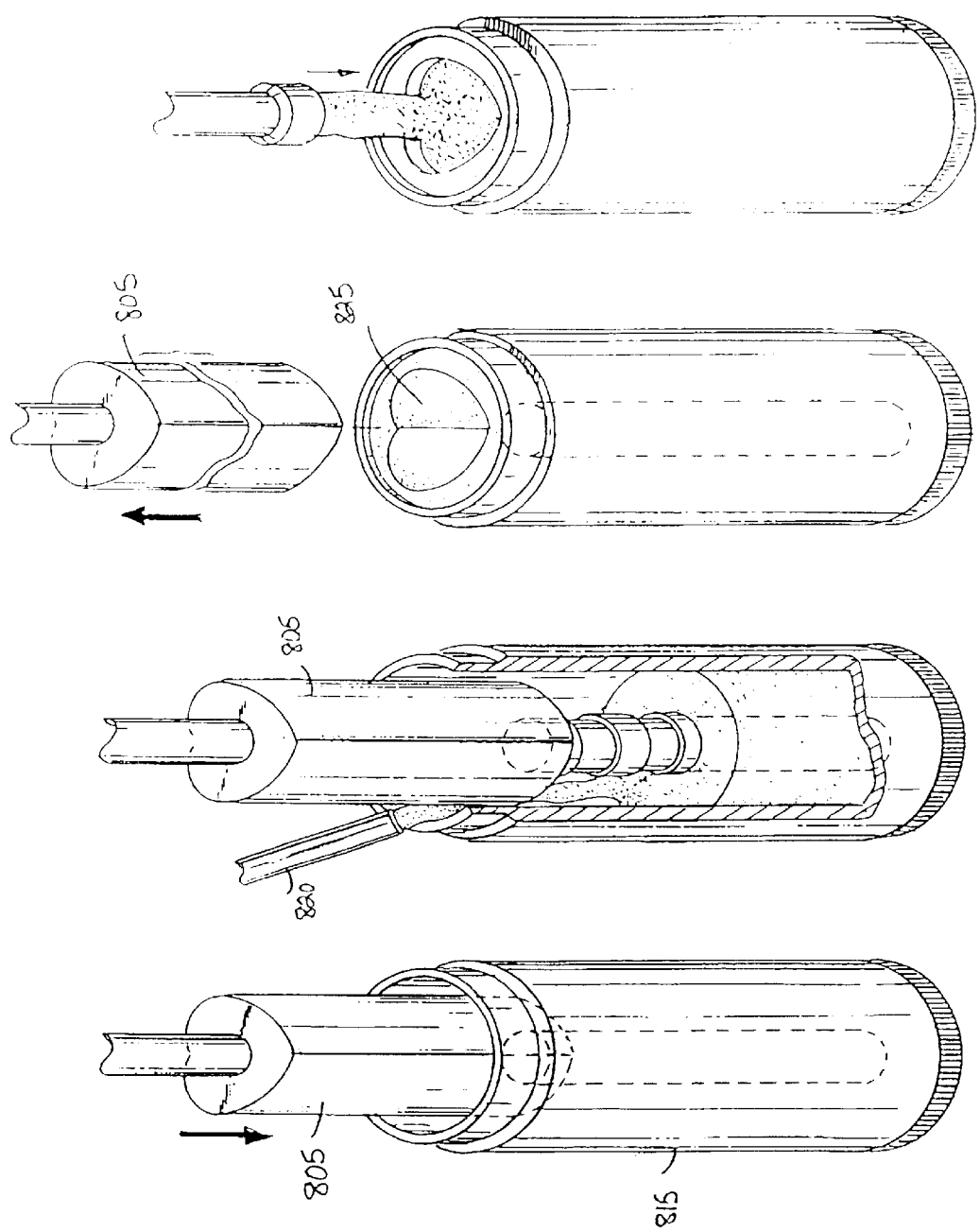

MULTI-COMPOSITION STICK PRODUCT AND A PROCESS AND SYSTEM FOR MANUFACTURING THE SAME

CROSS-REFERENCE TO RELATED APPLICATIONS

This application is a continuation-in-part of U.S. patent application Ser. No. 09/584,640 filed May 31, 2000, the entire disclosure of which is incorporated herein by reference.

FIELD OF THE INVENTION

The present invention relates to a multi-composition stick product comprising a molded stick composition, such as a lip balm, sun screen, deodorant, or glue stick, provided in a container which serves as the mold during manufacture and from which the composition may be advanced or ejected. The invention also relates to a process and system for manufacturing the stick product.

DESCRIPTION OF RELATED ART

Lip balms, deodorants, sunscreens, and glue sticks, usually have a single homogenous color or fragrance. These products typically are aesthetically neutral or unpleasing. As a result, patients, in particular, children, often do not apply such topical products and, therefore, do not benefit from these products. For example, children often do not apply a sunscreen lip balm for protecting their lips before playing outside.

Therefore, it is desirable to develop lip balms, deodorants, sunscreens, glue sticks, and related products which are aesthetically pleasing to increase use of such products and consumer/patient compliance.

Additionally, since lip balm compositions are often the same homogenous color and fragrance, patients often cannot identify one lip balm formulation from another. For example, a patient having a lip balm with a sunscreen, e.g., paba, and another without sunscreen, needs to be able to readily distinguish the two products from one another. Similarly, it would be desirable to easily identify any specific type of lip balm, deodorant, sunscreen, glue stick, or related product.

Homogenous compositions may be manufactured using conventional techniques, such as a nozzle fill or flood fill method. In the nozzle fill method a homogeneous composition is dispensed from a filling nozzle directly into the container itself, whereas in the flood fill method the container is placed in an opening of a tray and the composition is poured onto the tray thereby flooding the tray and, in turn, filling the container. These conventional techniques, however, are not suitable for use in manufacturing a multi-composition stick product, that is, a stick product which contains two or more compositions.

Methods have been developed for use in manufacturing multi-color lipsticks that are manufactured in a mold and then removed and transferred to a separate container. In such products the composition does not contact the walls of the container in which the product is ultimately disposed. For example, U.S. Pat. No. 4,291,018 discloses a method for manufacturing a lipstick having a construction of the core-sheath type which comprises two different compositions arranged as an inner core surrounded by an outer sheath. The formation of a core-sheath type lipstick is realized using a molding body having an upper part and a lower part. A rod is inserted into the molding body and then the molten mass of the lipstick composition for the molding of the sheath is poured into the cavity and cooled to form the sheath portion around the rod. Then the rod and upper part of the molding body are removed thereby forming a core cavity. The upper part is remounted and a molten mass of the composition for the molding of the core is poured into the core cavity and cooled to solidify the composition. Thereafter, the upper part is demounted and the molded product is removed from the lower part and mounted in a suitable case to obtain a lipstick. As a finished product the lipstick does not contact the inner walls of the container.

U.S. Pat. No. 4,743,443 discloses a method for manufacturing a tri-color lipstick divided into three parallel laminae. A T-shaped centrally disposed insert is placed in a cylindrical cavity main body portion of a mold. First and third laminae are poured while maintaining a space for the later pouring of the second intermediate lamina. Thereafter, the insert is removed and the second intermediate lamina is poured. The tri-color lipstick is then removed from the mold and disposed so as not to contact the inner walls of the container.

U.S. Pat. Nos. 4,786,449 and 4,602,886 teach manufacturing a multi-color marking implement in a transparent lipstick type container that also serves as the mold during the casting process. A variegated color pattern is built up by dispensing different color compositions, dropwise, into the container. The elimination of the use of a mold between colors allows mixing at the interface between adjacent colors, thereby forming a random design. The dropwise method used to generate a random pattern is also disadvantageously slow.

It is therefore desirable to develop a multi-composition stick product in which the compositions, which preferably differ in at least one component, e.g., color, are arranged in a predetermined non-random pattern that is reproducible, and to develop a method and apparatus for manufacturing the same.

SUMMARY OF THE INVENTION

The present invention provides a multi-composition stick product comprising a container and a molded stick composition disposed so as to contact the walls of the container and be advanceable in the container. The stick composition comprises a first composition and a second composition. The first and second compositions differ in at least one component, i.e., the first or second composition contains a component which is not contained in the other composition, and are arranged in a predetermined non-random pattern that is reproducible.

Also disclosed is a method for manufacturing a multi-composition stick product as described above. A mold shaft is first inserted into the container and a first composition of stick composition is dispensed into the container around the mold shaft. The mold shaft is then removed from the container to form a cavity and at least a portion of the cavity is filled with a second composition of stick composition.

In another embodiment of a method for manufacturing the multi-composition stick product in accordance with the present invention a first composition of stick composition is dispensed into the container. While the first composition is in a molten state, a mold shaft is then inserted into the container so as to displace the first composition therein. Once the first composition is sufficiently solidified, the mold shaft is removed from the container to form a cavity. Finally, at least a portion of the cavity is filled with a second stick composition.

Furthermore, the invention is directed to a system for carrying out the method described above. The system includes a filling nozzle including a mold shaft insertable into the container and an outer barrier disposed about at least a portion of the mold shaft so as to form a passageway between the outer barrier and the mold shaft for receiving the first composition.

According to a special aspect of this invention, a stick product is provided comprising a container and a molded stick composition disposed so as to contact the walls of the container and be advanceable in the container. The container confers a desired shape or design to the stick composition and the stick product. At least a portion of the outer and/or inner contour of the container is non-circular. For example, the outer and inner contours of the container may be heart shaped. Alternatively, the outer contour of the container may be heart shaped while the inner contour is circular or vice versa. In this embodiment, the stick composition may have only one phase (homogeneous) or two or more distinct phases.

An alternative embodiment of a system in accordance with the present invention for simultaneously dispensing the first and second compositions includes a first filling nozzle for dispensing the first composition and a second filling nozzle for dispensing the second composition. The first and second filling nozzles are connected together using a securing mechanism and, when assembled are capable of being inserted together into the container.

BRIEF DESCRIPTION OF THE DRAWINGS

The foregoing and other features of the present invention will be more readily apparent from the following description and drawings of illustrative embodiments of the invention wherein like reference numbers refer to similar elements throughout the several views and in which:

FIG. 1a is a perspective view of an exemplary multi-composition stick product advanced from its container in accordance with the present invention;

FIG. 1b is a cross-sectional view of the multi-composition stick product of FIG. 1a along the line 1b—1b;

FIG. 1c is a cross-sectional view of the multi-composition stick product of FIG. 1a along the line 1c—1c;

FIG. 1d is a perspective view of a multi-composition stick product advanced from an exemplary container having the same inner and outer heart shaped contour;

FIG. 1e is a perspective view of a multi-composition stick product advanced from an exemplary container having a cylindrical outer contour and a heart shaped inner contour;

FIGS. 3a–3d show the operating steps of a first embodiment of an exemplary nozzle fill system for manufacturing a multi-composition stick product in accordance with the present invention;

FIGS. 7a–7d show the operating steps of a third embodiment of an exemplary nozzle fill system for manufacturing a multi-composition stick product in accordance with the present invention;

FIG. 8a is a side view of an exemplary multi-nozzle fill system in accordance with the present invention before being inserted in a container;

FIG. 8b is a side view of the exemplary multi-nozzle fill system in FIG. 8a after being inserted in the container;

FIG. 8c is a bottom view of the multi-nozzle along line 8c—8c in FIG. 8a;

DETAILED DESCRIPTION OF THE INVENTION

Figure 2:
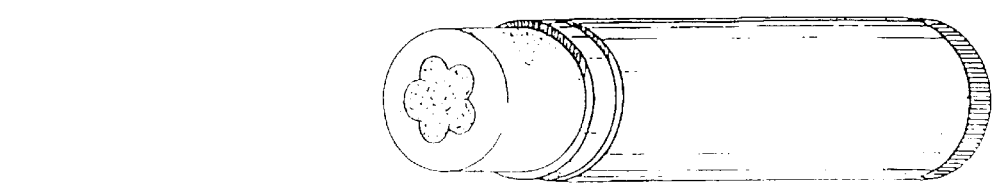
FIGS. 2a through 2x are perspective views of exemplary predetermined patterns formed by the composition stick.
Figure 2:
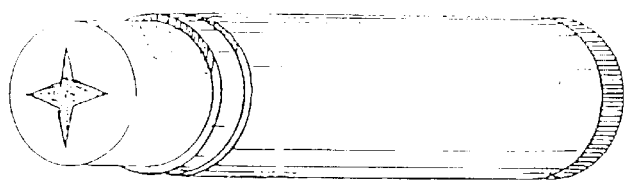
Figure 2:
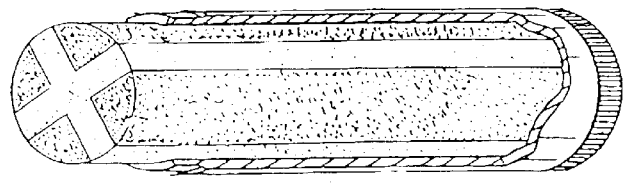
Figure 2:
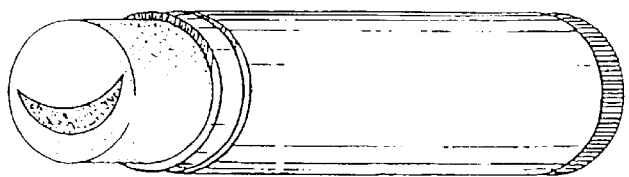
Figure 2:
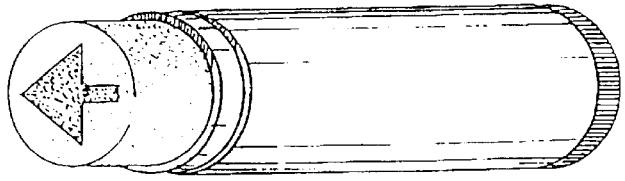
Figure 2:
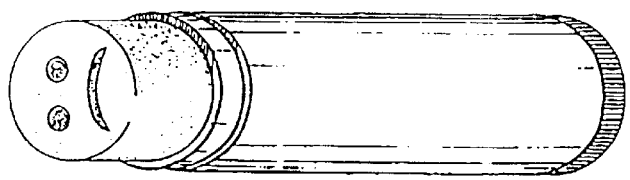
Figure 2:
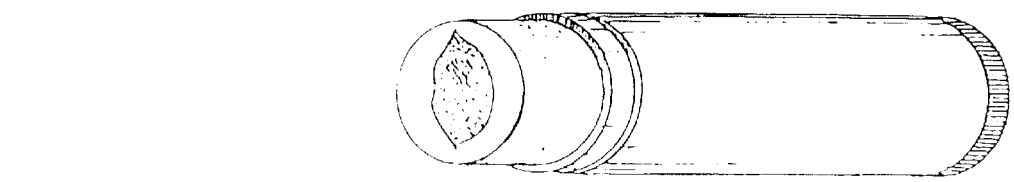
Figure 2:
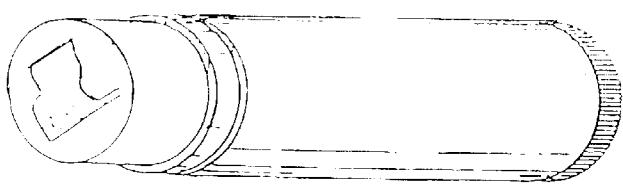
Figure 2:
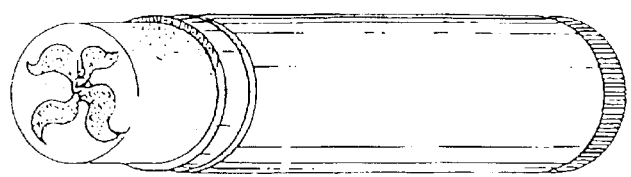
Figure 2:
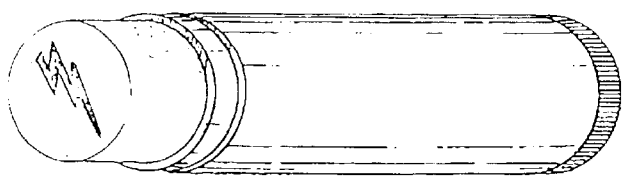
Figure 2:
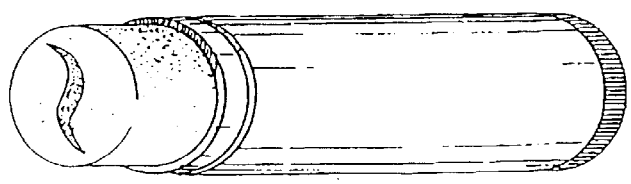
Figure 2:
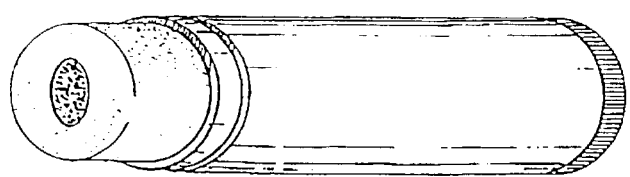

In the application the following terms are defined. The term "stick product" is defined as a product comprising a container and a stick composition, where the stick composition is: (a) manufactured directly in the container in which it is sold, so that the container also serves as a mold during the casting process, whereby the composition is in contact with the side walls of the container, and (b) advanced or ejected, such as by mechanical rotation or mechanical force without rotation, through an open end of the container. The term "stick composition" is defined as a malleable, semi-solid composition that is sufficiently solid so as to substantially retain its shape when advanced or ejected from an open end of the container, while capable of leaving a desired residue when applied by swiping.

By way of example, the multi-composition stick product in accordance with the present invention, as well as the apparatus and method for manufacturing the same, is shown and described for a multi-color stick composition disposed in a cylindrical housing or container and forming a predetermined design pattern comprising a heart shaped first composition core by a second composition sheath.

FIG. 1a is a perspective view of an example multi-composition stick product 10 advanced in the container. The multi-composition stick product 10 comprises a container 12 and a molded stick composition 14 disposed so as to contact the walls of the container and be advanceable in the container. The stick composition in FIG. 1a comprises a first composition and a second composition. It is, however, within the intended scope of the invention for the stick composition to comprise more than two compositions. The first and second compositions are preferably chemically similar materials. In a preferred embodiment, the top surface 16 of the stick composition 14 is substantially planar.

The term "chemically similar materials" as used herein is defined as materials which have substantially the same physical, chemical and/or medicinal properties under ambient conditions, but which differ in a component or components that result in two or more distinct or distinguishable phases of the composition. The different "component" refers to, for example, a medicament; colorant; fragrance; flavorant; sunscreen; preservative; conditioner, such as a skin conditioning agent; moisturizer; emollient; or surfactant. For example, one composition may have one color while the other composition has a different color. Generally, such a component will comprise less than about 20% by weight, preferably less than about 5% by weight, and more preferably, less than about 1% by weight of the composition in which it is found, based upon 100% by weight of total composition.

The outer and inner contours of the container may be any desired shape, such as cylindrical, square, triangular, or heart shape. The outer and inner contours of the container may be the same, or different, from one another. For example, in FIG. 1d the inner and outer contour of the container are the same heart shape, whereas in FIG. 1e the container has a cylindrical outer contour and a heart shape inner contour.

Preferably, the container is made of a transparent or translucent material so that the consumer may view the predetermined non-random pattern formed by the stick composition through the container.

The compositions of the stick composition disposed in the container are arranged in a predetermined non-random pattern that is reproducible. Any desired pattern may be selected, for example, a heart (FIGS. 1a–1d); evergreen tree (FIG. 2a); ying-yang (FIG. 2b); 5-pointed star (FIG. 2c); 6-pointed star (FIG. 2d); sun (FIG. 2e); circle (FIG. 2f); half and half circle (FIG. 2g); heart with an arrow (FIG. 2h); lateral stripes (FIG. 2i); diagonal stripes (barber pole) (FIG. 2j); longitudinal stripes (FIG. 2k); happy face (FIG. 2l); sad face (FIG. 2m); tree (FIG. 2n); crescent moon (FIG. 2o); cross (FIG. 2p); 4-pointed star (FIG. 2q); flower (FIG. 2r); ellipse (FIG. 2s); wave (FIG. 2t); lightening bolt (FIG. 2u); pinwheel (FIG. 2v); flag (FIG. 2w); lips (FIG. 2x); one or more alphanumeric letters; any other geometric shape, such as a polygon; or any combination of the foregoing. An infinite number of different permutations are possible by varying the outer and/or inner contour of the container and/or predetermined non-random pattern of the stick composition within the container. Each cross-section perpendicular to the longitudinal axis of the stick composition may contain the same multicolor image (e.g., for a heart image) or a different multicolor image (e.g., for an image having horizontal or diagonal stripes). Preferably, there is little, if any, intermixing at the interface of the compositions so as to maintain the integrity of the predetermined non-random pattern.

In one embodiment, the stick composition is a lip balm, in which one composition of the stick composition contains a sunscreen while the other does not. These two compositions can be arranged, e.g., in a half circle pattern, as shown in FIG. 2g, or in a ying-yang pattern, as shown in FIG. 2b. This permits a user to apply lip balm with and without sunscreen. For example, the sunscreen-free composition may be applied when the user is indoors, while the sunscreen composition may be applied when the user is outdoors. The sunscreen-containing composition preferably has a different color than the non-sunscreen-containing composition.

According to another embodiment, to facilitate manufacture the stick composition has a first composition or phase having a melting point greater than that of the second composition or phase. Introduction of the second phase, at a lower temperature will avoid or minimize melting of the first composition, thus optimizing the design integrity by minimizing mixing at the interface of the two compositions. The melting point of the first composition may be increased by, for example, adding additional carnauba wax. Preferably, the melting point of the first composition is at least about 5° C. and more preferably about 10° C. greater than that of the second composition. According to a preferred embodiment, the first composition or phase has a melting point greater than about 60° C. and the second composition or phase has a melting point of less than about 60° C.

In another embodiment, two compositions having the same or substantially the same melting point may be used, wherein the second composition is dispensed in the container, after the first composition has been dispensed into the container and cooled. The same design integrity can be achieved by cooling the first composition to a sufficiently low temperature so that when the second composition in its molten (liquid or fluid) state at substantially the melting point temperature is dispensed into the container little, if any, intermixing occurs at the interface between the two compositions.

In yet another embodiment, the melting point of the second composition may be higher than the first composition. The first composition is cooled to a temperature, lower than that disclosed above when the two compositions have substantially the same melting point, before the second composition is dispensed into the container. The second composition, when dispensed into the container, is maintained at a temperature substantially equal to its melting point. The temperature of the first composition is selected to ensure design integrity with little, if any, mixing of the two compositions when the second composition is dispensed into the container at a temperature. Therefore, design integrity can be realized irrespective of whether the melting point of the two compositions is the same or different.

Preferably, one composition contains at least one colorant which is not contained in the other composition. In other words, in a preferred embodiment the first and second compositions differ in color. The term "color" is defined for the purpose of the description of this invention to include clear, transparent, opaque, as well as any other color, shade or tone of the color spectrum. Any number of two or more colors may be used as desired. In such an embodiment, the compositions form a discrete multicolor predetermined image, i.e., an image including two or more colors. Preferably, the colorants are selected to provide good contrast and be eye catching. For example, the stick composition may contain a red composition and a green composition to form an image of a red heart with a green background. Attractive, traditional, holiday or national color combinations are well-known in the art and, though it is not limited to any particular combinations, desirable for the present invention.

The image may be, for example, a red heart on a white or pink field (the term "field" refers to the background, which is the stick composition encasing a specific image shape); a green evergreen tree on a red field; a yellow and purple ying-yang; a red or white 5-pointed star on a blue field; a yellow or white 6-pointed star on a blue field; a yellow sun on a blue field; a red circle on a white field; blue and orange half and half circle; a red heart with an arrow on a white field; pink and green lateral stripes; red and blue or white diagonal stripes (barber pole); red and green longitudinal stripes; a happy face on a yellow field; a sad face on a green or blue field; an orange tree on a brown field; a white crescent moon on a blue field; a red cross on a blue or white field; a white 4-pointed star on a blue field; a pink flower on a green field; a green ellipse on a yellow field; a white wave on a blue field; a yellow lightening bolt on a blue field; a yellow or pink pinwheel on a red, green, or blue field; a green flag on a white field; red lips on a white, pink, or brown field; one or more alphanumeric letters; any other geometric shape, such as a polygon; or any combination of the foregoing.

The only constraint on the number of colors and design pattern selected is that of the size of the container and the desire to maintain the different color compositions discrete from each other so as to substantially prevent mixing at the interface between colors and maintain the integrity of the predetermined image.

Although, the first and second compositions contain colorants, the compositions preferably become transparent or translucent when swiped or applied onto a substrate. Typically, the compositions become transparent or translucent due to the thinness of the film formed or a property of the compositions.

Suitable colorants include, but are not limited to, those approved by the U.S. Food and Drug Administration for application to the skin and lips, such as FD&C colors and D&C colors. Examples of such colorants include, but are not limited to, Red-6 Ca, Red-6 sodium, titanium dioxide, red iron oxide, Red 21, and Red 27. Preferably, the colorants, such as white, yellow, red, and orange colorants, do not fade upon extreme sun exposure.

The colorant may also be a color changing agent. Color changing agents include agents which change their color and spectroscopic properties in the visible light and/or ultraviolet spectra, or in response to other stimuli. Preferred color changing agents include, but are not limited to, those which change their color in the visible light spectrum. Color changing agents may be activated by, for example, moisture and pH. For example, a color changing agent may exhibit one color in a moisture-free environment and a second color when in contact with water. The color changing property of the agent may be reversible or irreversible, i.e., the color changing agent may or may not revert back to its original color after being activated and deactivated. Preferably, the color changing agent reverts back to its original color after activation and deactivation. When a color changing agent is activated, a multi-colored predetermined reproducible image appears, disappears, or changes color. The image may be any of the aforementioned images. Color changing agents which are included in stick compositions intended for topical application typically are non-toxic to the skin and safe to digest.

Suitable color changing agents which are moisture and/or pH activated, include but are not limited to, D&C Red 21, D&C Red 27, and any combination of any of the foregoing.

The stick composition may be a composition intended for topical application to a person, such as a lip balm, lipstick, lip gloss, deodorant, or sunscreen, or other composition, such as a glue stick. The stick composition is sufficiently solid to substantially retain its shape when advanced or ejected from the container.

Lip Balms

Generally, lip balm stick compositions for topical application comprise a wax or other pharmaceutically acceptable vehicle and, optionally, one or more medicaments and/or adjuvants. Suitable waxes include, but are not limited to, petrolatum wax; carnauba wax; paraffin wax; white wax; candelilla wax; beeswax; oils, such as arachidyl propionate, cetyl alcohol, isopropyl lanolate, isopropyl myristate, lanolin, mineral oil, light mineral oil, octyldodecanol, oleyl alcohol, ethyl macadamiate, castor oil, jojoba esters, hydrogenated castor oil, hydrogenated vegetable oil, cetyl ricinoleate, propylene glycol, isopropyl palmitate, stearyl alcohol, and volatile and non-volatile silicone oils; and any combination of any of the foregoing. Suitable silicone oils include, but are not limited to, polyphenylmethyl siloxane, dimethicone, cyclomethicone, and any combination of any of the foregoing.

Suitable minor components include, but are not limited to, sunscreens (which will also be found in a sunscreen stick), such as octyl methoxycinnamate, octyl dimethyl p-aminobenzoate, actinoquinol, p-aminobenzoic acid, butyl methoxydibenzoylmethane, beta-carotene, 4-dimethylamino benzoic acid, dioxybenzone, drometrizole, lawsone, sulisobenzene, titanium dioxide, and zinc oxide; preservatives, such as parabens, including but not limited to, methylparaben, isopropylparaben, and isobutylparaben; flavorants; fragrances; colorants, such as beta-carotene; conditioners, such as skin conditioning agents, including but not limited to, the aforementioned waxes and oils, especially petrolatum, dimethicone, and polymethylsiloxane; moisturizers; emollients; cleansing agents; antioxidants, such as tocopherol; antistatic agents, such as cocamidopropyl PG-dimonium chloride; stabilizers; and pH adjusters, such as sodium hydroxide and hydrochloric acid. Preferably, each such component is approved for use in or on humans by the Food and Drug Administration, or corresponding regulatory bodies in other regions or countries.

Suitable lip balm stick bases for the first and second compositions are shown in Tables 1–6 below.

TABLE 1

Exemplary Lip Balm Formulation Compositions 1 and 2

| Component | Lip Balm Formulation 1 (% w/w) | Lip Balm Formulation 2 (% w/w) |
|---|---|---|
| White Petrolatum USP | 45.8 | 45.2 |
| Arachidyl Propionate | 3 | 3 |
| Camphor | 0.8 | 0.8 |
| Carnauba Wax | 1 | 1 |
| Lanolin | 5 | 5 |
| Light Mineral Oil | 15 | 15 |

TABLE 1-continued

Exemplary Lip Balm Formulation Compositions 1 and 2

| Component | Lip Balm Formulation 1 (% w/w) | Lip Balm Formulation 2 (% w/w) |
|---|---|---|
| Octyldodecanol | 5 | 5 |
| Oleyl Alcohol | — | 2 |
| Paraffin Wax | 20.4 | 20.5 |
| White Wax | 2 | 2 |
| Chapstick Color Mix D&C Red #6 Barium Lake | 0 | 0.25 |
| Flavor | 2 | 0.25 |

Using formulation 1 as the first composition, and formulation 2 as the second composition, two color lip balm designs can be prepared as described above. Moreover, the lighter colored composition (formulation 1) has more flavor.

TABLE 2

Lip Balm Formulation Composition 3

| Component | % w/w |
|---|---|
| Vegetable Oil, Hydrogenated Vegetable Oil, and/or Candelilla Wax | 73.2 |
| Hydrogenated Vegetable Oil | 13 |
| Shea Butter Extract | 2 |
| Beeswax | 7.8 |
| Carnauba Wax | 3.8 |
| Flavor | 0.02 |

TABLE 3

Lip Balm Formulation Composition 4

| Component | % w/w |
|---|---|
| Ethyl Macadamiate | 20 |
| Jojoba Esters | 1 |
| Carnauba Wax | 5.1 |
| Candelilla Wax | 5.1 |
| Beewax | 3 |
| Hydrogenated Castor Oil | 1 |
| Cetyl Ricinoleate | 2 |
| Isopropylparaben, Isobutylparaben, and/or Butylparaben | 0.1 |
| Titanium Dioxide and/or Hybrid Sunflower Oil | 3 |
| Beta-carotene (30%) | 0.03 |
| Octyl Methoxycinnamate | 5 |
| Tocopherol | 0.5 |
| Flavor | 2 |
| Castor Oil | qs |

TABLE 4

Lip Balm Formulation Composition 5

| Component | % w/w |
|---|---|
| Dimethicone NF | 2 |
| Cetyl Alcohol NF | 6 |
| Silicon Dioxide NF | 0.2 |
| Cyclomethicone | 7 |
| Colorant | 0.15 |
| Hydrogenated Polyisobutene[1] | 10 |
| Isocetyl Sterate | 20.4 |
| Methylparaben NF | 0.1 |
| Microcrystalline Wax | 25 |
| Propylparaben NF | 0.1 |
| Vitamin A Palmitate USP | 0.1 |
| Vitamin E Acetate USP | 1 |

TABLE 4-continued

Lip Balm Formulation Composition 5

| Component | % w/w |
|---|---|
| Regent Petrolatum USP | 27 |
| Aloe Vera Oil-Filtered | 1 |

[1]Hydrogenated Polyisobutene is available as Panalane H-300 from Amoco Chemical Co. of Chicago, IL.

TABLE 5

Lip Balm Formulation Composition 6

| Component | % w/w |
|---|---|
| Petrolatum Penreco Amber USP | 45 |
| Arachidyl Propionate | 3 |
| Carnauba Wax | 1 |
| Cocoa Butter NF | 5 |
| Isopropyl Lanolate | 1.5 |
| Mineral Oil Light NF | 14 |
| Octyldodecanol NF | 4.5 |
| Oleyl Alcohol | 1.75 |
| Wax Paraffin | 21.75 |
| White Wax NF | 2.5 |

[2]Polyphenylmethylsiloxane is available as Dow Corning 556 fluid from Dow Corning of Dow Chemical USA of Midland, MI.

TABLE 6

Lip Balm Formulation Composition 7

| Component | % w/w |
|---|---|
| White Wax | 2 |
| Carnauba Wax | 1 |
| Isopropyl Myristate | 1 |
| Wax Paraffin | 22 |
| Oxybenzone | 3.5 |
| White Petrolatum | 42 |
| Isopropyl Lanolate | 1.8 |
| Octyl Methoxycinnamate | 7.5 |
| Octyldodecanol | 4.7 |
| Light Mineral Oil | 12 |
| Flavor | 2.5 |

Other suitable lip balm bases for the first and second compositions include, but are not limited to, those described in *Cosmetic and Toiletry Formulations, Cosmetic and Toiletry*, Vol. 1, pp. 166, 488–489 (1989), which are herein incorporated by reference.

Sunscreen Sticks

The sunscreen stick compositions of the invention are analogous to the lip balm compositions. However, sunscreen sticks may use different waxes and active ingredients.

Suitable waxes for sunscreen compositions include, but are not limited to, the waxes for lip balms above.

The sunscreen composition will include a sunscreen, such as octyl methoxycinnamate, octyl dimethyl p-aminobenzoate, actinoquinol, p-aminobenzoic acid, butyl methoxydibenzoylmethane, beta-carotene, 4-dimethylamino benzoic acid, oxybenzone, dioxybenzone, drometrizole, lawsone, sulisobenzene, titanium dioxide, zinc oxide, and any combination of any of the foregoing. Suitable sunscreens and their absorbance ranges and approved concentrations are shown in Table 7 below.

TABLE 7

Sunscreen Ingredients

| Component | Absorbance Range (nm) | Approved Concentration (% w/w) |
|---|---|---|
| Amino benzoic acid | 260–313 | 5–15 |
| Glyceryl aminobenzoate | 264–315 | 2–3 |
| Padimate O | 290–315 | 1.4–8 |
| Ethyl 4-[bis(hydroxypropyl)] aminobenzoate | 280–330 | 1–5 |
| Methyl anthranilate | 260–380 | 3 |
| Dioxybenzone | 260–380 | 3 |
| Oxybenzone | 270–350 | 2–6 |
| sulisobenzone | 260–375 | 5–10 |
| Cinoxate | 270–328 | 1–3 |
| Diethanolamine methoxycinnamate | 280–310 | 8–10 |
| Octyl methoxycinnamate | 290–320 | 2–7.5 |
| Octocrylene | 250–360 | 7–10 |
| Avobenzone | 320–400 | 3 |
| Octyl salicylate | 280–320 | 3–5 |
| Homosalate | 295–315 | 4–15 |
| Trolamine salicylate | 260–320 | 5–12 |
| Digalloyl trioleate | 270–320 | 2–5 |
| Lawsone with dihydroxyacetone (DHA) | 290–400 | 0.25 (Lawsone), 3 (DHA) |
| Phenylbenzimidazole sulfonic acid | 290–320 | 1–4 |
| Red petrolatum | 290–365 | 30–100 |
| Titanium dioxide | 290–770 | 2–25 |
| Zinc oxide | ~200–390 | 2–25 |

Preferred sunscreens include, but are not limited to, octyl methoxycinnamate and oxybenzone.

Preferred minor components of the sunscreen composition include a medicament; colorant; fragrance; and conditioner.

Stick Deodorants

The deodorant stick compositions of the invention are analogous to the lip balm and sunscreen compositions. However, deodorants use different waxes and active ingredients. Moreover, according to this aspect of the invention, a deodorant gel and "white" solid deodorant/antiperspirant can be used as the different compositions.

Typical compounds (high molecular weight hydrocarbons, alcohols, and acids) included in deodorant compositions include, but are not limited to, stearic acid, stearyl alcohol, propylene glycol, cyclomethicone, and any combination of any of the foregoing.

The deodorant compositions will also include one or more deodorants, such as (though not limited to) cocamidopropyl PG-dimonium chloride phosphate, abietic acid, aluminum citrate, aluminum PCA, azadirachta indicia extract, chlorophyllin-copper complex, eugenia jambolana extract, farnesol, fermented vegetable extract, ginger lily (*Hedychium spicatum*) extract, α-glucan-oligosaccharide, mauritia flexosa extract, octoxyglycerin, salvia miltiorrhiza extract, sandalwood (*Santalum album*) extract, sodium aluminum chlorohydroxy lactate, spondias amara extract, triethyl citrate, zinc phenolsulfonate, zinc ricinoleate, and any combination of any of the foregoing. They may also, or alternatively, contain one or more antiperspirants, including, but not limited to, allantoin-aluminum chlorohydrate, aluminum capryloyl hydrolyzed collagen, aluminum chlorhydrex GLY, aluminum chloride, aluminum chlorohydrate, aluminum chlorohydrex, aluminum PCA, aluminum sesquichlorohydrate, aluminum undecylenoyl collagen amino acids, aluminum zirconium pentachlorohydrate, aluminum zirconium tetrachlorohydrate, aluminum zirconium tetrachlorohydrex GLY, aluminum zirconium trichlorohydrate, aluminum zirconium pentachlorohydrate, sage (*Salvia officinalis*) extract, tormentil (*Potentilla erecta*) extract, zirconium chlorohydrate, and any combination of any of the foregoing.

Preferred minor components of the stick deodorant composition include a medicament; colorant; fragrance; and conditioner.

Suitable deodorant formulations for the first and second compositions are shown in Tables 8 and 9 below.

TABLE 8

Deodorant Formulation 1

| Component | % w/w |
|---|---|
| Stearic Acid | 8 |
| Ethanol | 73.6 |
| Propylene Glycol | 10 |
| Isopropyl Palmitate | 5 |
| Cocamidopropyl PG-dimonium Chloride Phosphate | 1 |
| Sodium Hydroxide (50%) | 2.4 |

TABLE 9

Deodorant Formulation 2

| Component | % w/w |
|---|---|
| Cyclomethicone | 45 |
| Stearyl Alcohol | 19 |
| Dimethcone | 5 |
| Aluminum Zirconium Tetrachlorohydrex GLY | 22 |
| Talc | 4 |
| Mineral Oil | 2 |
| Hydrogenated Castor Oil | 3 |
| Fragrance | qs |

Glue Sticks

Generally, glue sticks comprise an adhesive. Suitable adhesives include, but are not limited to, starches; dextrins; cellulose ethers, such as methyl cellulose and carboxymethyl cellulose; starch ethers; and any combination of any of the foregoing. Glue sticks may further comprise binders, such as poly(vinyl pyrrolidone), and minor ingredients. Examples of suitable adhesive stick formulations are described in U.S. Pat. Nos. 5,371,131; 5,433,775; and 5,965,657.

Manufacturing Methods and Systems

By way of example, the systems and method for manufacturing the multi-composition stick product in accordance with the present invention will now be described in detail for a specific embodiment of a multi-composition stick product wherein the image is a heart. The heart shaped image in FIGS. 3a–3d is different than that shown in FIGS. 1a–1d in that the sides are curved instead of straight. An example nozzle fill system in accordance with a first embodiment of the present invention, is shown in FIGS. 3a–3d, for filling a single container. The nozzle fill system includes a container or housing 100 and one or more filling nozzles 110. Container 100 preferably has a container screw 105 projecting upwards from its bottom and a lip 107. The container screw 105, when rotated, advances the composition through the open end of the container 100. Alternatively, a container shaft projecting from a false bottom may be placed in the bottom of the container, whereby a mechanical force imposed on the false bottom advances the stick composition from the open end of the container. The use of a container shaft or container screw may be eliminated altogether, whereby the stick composition is advanced through the open end of the container by imposing a force on a false bottom of the container.

In the example shown in FIGS. 3a–3d, the container 100 has a cylindrical outer contour and a cylindrical inner contour. One or more nozzles 110 are used, in series, to fill the container 100 with the stick composition. The nozzle 110 includes a mold shaft 115 fixedly connected to an outer barrier or shield 120 having an inlet nozzle 125 connected to a supply source through which the first composition in a liquid state is received, as shown in FIG. 3b. Mold shaft 115, is preferably concentric with and extends beyond the outer barrier 120 in a longitudinal direction. In FIG. 3a, the exemplary mold shaft 115 has an outer contour in the shape of a heart. Mold shaft 115 may be solid, semi-hollow, or hollow. The term "semi-hollow" is defined as a shaft which is divided in a longitudinal direction into a hollow lower portion to be inserted into the container and a solid upper portion. Preferably, the mold shaft 115 is hollow or semi-hollow so as to receive the container screw, when inserted into the container 100.

Operation of the nozzle filling system shown in FIGS. 3a–3d will now be described in detail. First, in FIGS. 3a and 3b, the mold shaft 115 is inserted into the container 100. Mold shaft 115 may be inserted so that it contacts the closed end of the container 100 or, alternatively, may be inserted only into a portion of the container, e.g., halfway. As shown in FIG. 3b, a first composition in a liquid state (generally realized by heating the composition) is dispensed from the inlet nozzle 125 into a passageway, formed between the inner surface of the outer barrier 120 and outer surface of the mold shaft 115, and drips or flows into an outer region or area of the container 100 around the mold shaft 115. After filling the outer region or area a desired amount, for example, to the top of the container, the first composition is allowed to cool and solidify. Then the mold shaft 115 of the filling nozzle is removed from the container 100 leaving a solid outer region having an inner cavity 130 complementary in shape to that of the mold shaft, as shown in FIG. 3c. In the example shown in FIGS. 3a–3d, mold shaft 115 is hollow. The same filling nozzle 110 may therefore be used to fill the container 100 with both the first and second compositions. In FIG. 3a, a second supply source of the second composition in a liquid state is dispensed, either directly or indirectly via the top opening of the mold shaft 115, into the cavity 130 in the container formed by removal of the mold shaft. A top view of the filed container with the first and second compositions is shown in FIG. 3d. Finishing techniques, such as scraping or glazing, of the top surface of the composition stick may be performed after the container has been filed.

In an alternative configuration, wherein a solid or semi-hollow mold shaft 115 is used in accordance with the nozzle filling method described above, the second composition can not be dispensed through the top opening of the mold shaft 115. Therefore, with this arrangement a second filling nozzle having a hollow mold shaft may be used to fill the inner cavity 130 of the container with the second composition, or the second composition may be dispensed directly into the cavity of the container. After filling, the second composition is dispensed into the cavity it may be cooled by generating an air flow in the inlet nozzle.

Figure 5:
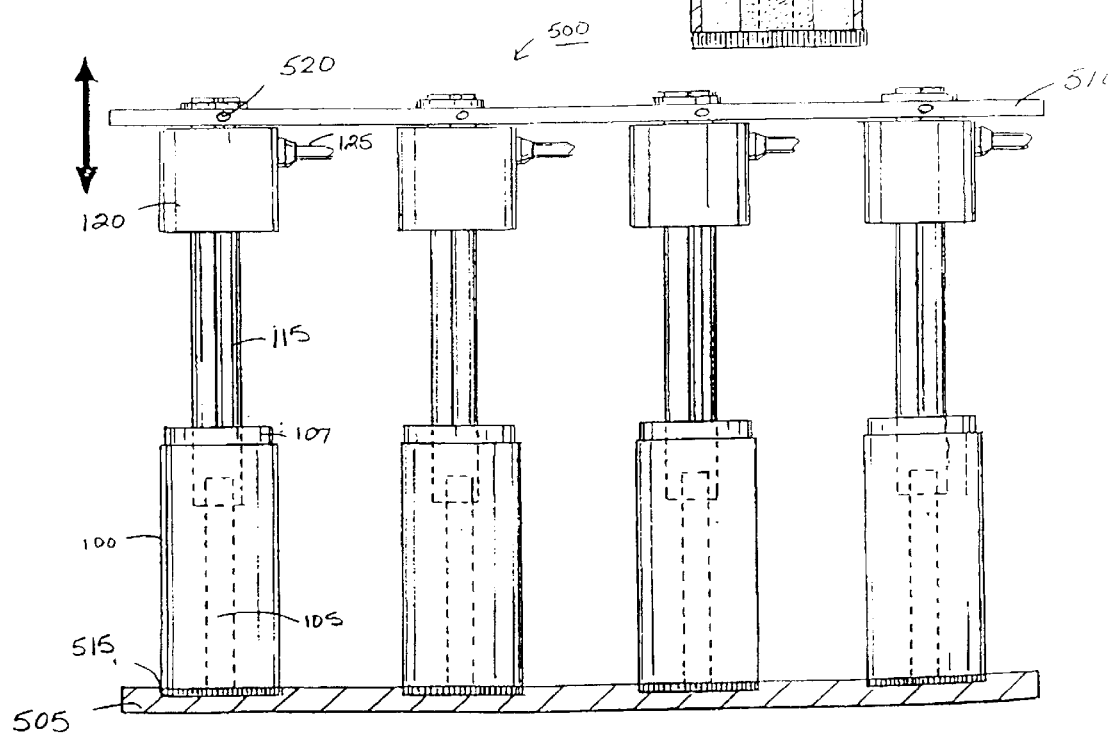
FIG. 5 is the nozzle fill system in FIG. 3a modified for simultaneously manufacturing a plurality of multi-compositions stick products in accordance with the present invention.

FIGS. 3a–3d show only a single container or housing 100 being filled. FIG. 5 is an exemplary nozzle fill system 500 for simultaneously manufacturing a plurality of containers using the steps in FIGS. 3a–3d. By way of example, FIG. 5 shows four containers 100 each having an associated filling nozzle 110. The system can be modified, as desired, to simultaneously fill any number of containers. An array or plurality of containers are inserted in respective holes 515 of a supporting tray 505. A holding member 510 is capable of supporting an array or plurality of interchangeable filling nozzles via releaseable locking devices 520, such as a pin, clip or clamp. The arrangement of the holes 515 in the supporting tray 505 mirrors the arrangement of the releaseable locking devices 520 in the holding member, so that when the filling nozzles are installed and the holding member 510 is properly aligned with respect to the supporting tray 505, each of the filling nozzles is disposed above a container to be filled. The holding member 510 may be assembled with all, or less than all, of the available releaseable locking devices 520 receiving a filling nozzle, as desired. In addition, all or some of the plural filling nozzles inserted into the releaseable locking mechanisms may be the same or different. The system shown in FIG. 5 may be assembled so that less than all of the holes 515 receive containers. Operation of the system is the same when manufacturing a plurality of multi-composition stick products, as that described above in FIGS. 3a–3d with respect to a single multi-composition stick product.

Figure 4:
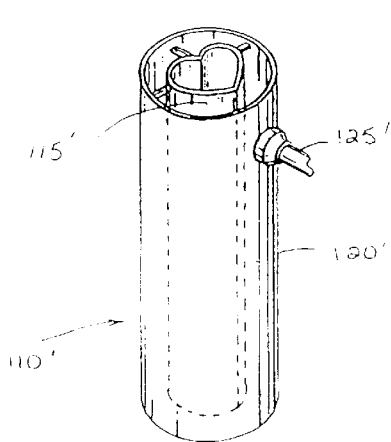
FIG. 4a is a perspective view of an alternative filling nozzle in accordance with the present invention.
FIG. 4b is a cross-sectional view of the filling nozzle in FIG. 4a inserted into a container.
Figure 4:
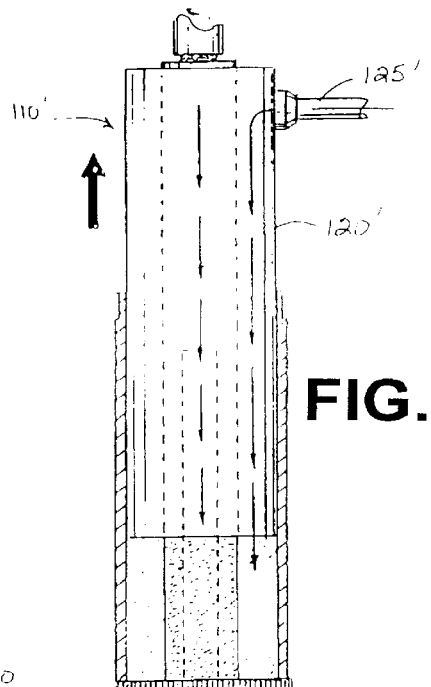

An exemplary alternative configuration of the nozzle fill system is shown in FIG. 4a. This embodiment is similar to that shown in FIG. 3a except that instead of the mold shaft 115 extending in a longitudinal direction beyond the terminating ends of the outer barrier 120, in FIG. 4a, the mold shaft 115' and outer barrier 120' are substantially equal in length. In operation the filling nozzle is inserted into the container, as shown in FIG. 4a. Thereafter, first and second compositions are simultaneously dispensed through the filling nozzle 110' as it is being raised from the container. Specifically, the first composition is dispensed through the inlet nozzle 125' while the second composition is dispensed through the top opening of the mold shaft 115'. The final image will be a heart shape with intermixing between the colors at the interface between two compositions.

Figure 6E:
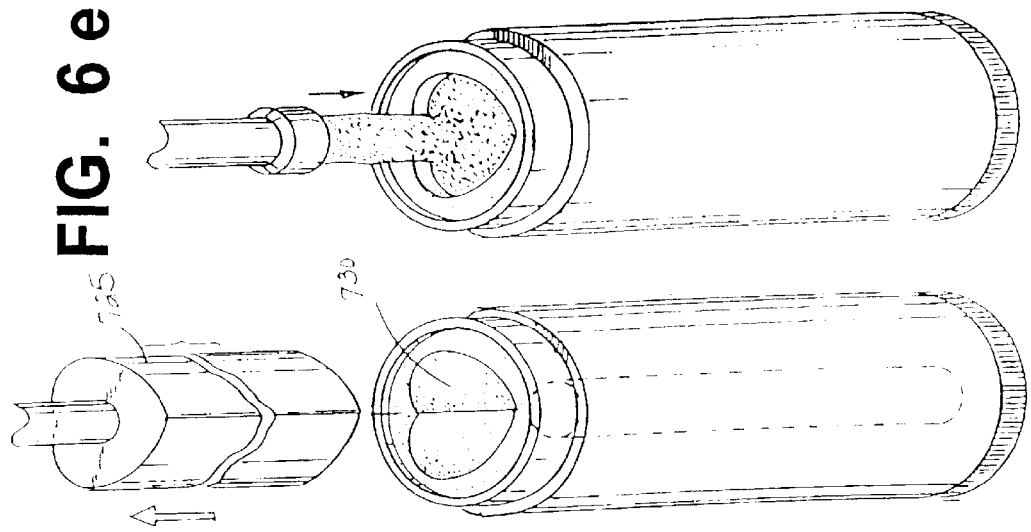
FIGS. 6a–6e show the operating steps of a second embodiment of an exemplary nozzle fill system for manufacturing a multi-composition stick product in accordance with the present invention.
Figures 6C, 6D:
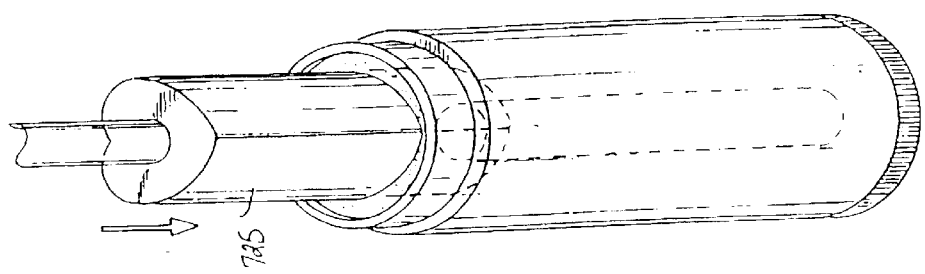
Figure 6B:
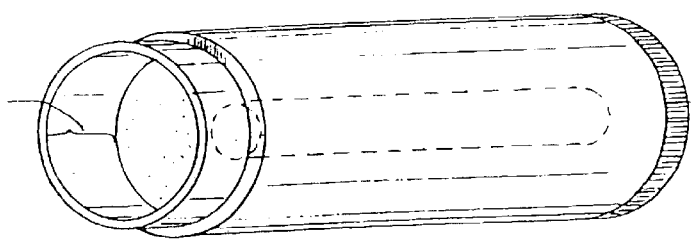
Figure 6A:
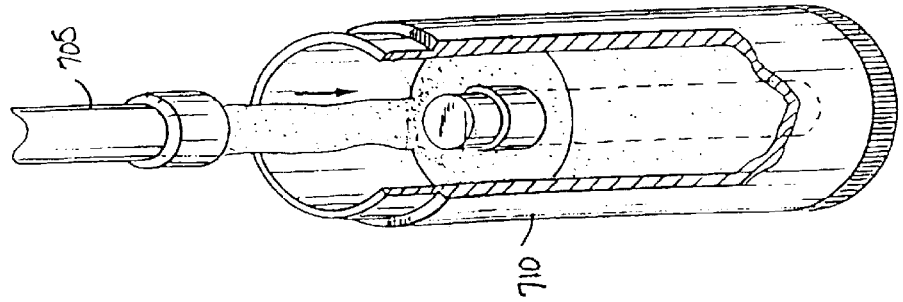

A third embodiment of an exemplary nozzle fill method for manufacturing a multi-composition stick product in accordance with the present invention is shown in FIGS. 6a–6e. Initially, in FIGS. 6a and 6b, the first composition is dispensed, for example, using an input nozzle 705, so as to partially fill the container 710 while leaving an air space 720 between the exposed surface of the first composition and the open end of the container. While the first composition is in a liquid state, a mold shaft 725 is inserted into a portion of the container 710 (FIG. 6c), thereby causing the first composition to be displaced and thus, rise in level in the container 710. Mold shaft 725 may be solid or have a closed end that when inserted into the container 710 causes the first composition to be displaced by and around the mold shaft 725. After the first composition has solidified, the mold shaft 725 is removed, thereby forming or leaving a cavity 730, as shown in FIG. 6d. The second composition in a liquid state is dispensed into the cavity 730, in FIG. 6e. Glazing or other finishing techniques may be performed on the top surface of the multi-composition stick.

FIGS. 7a–7d show a fourth embodiment of an exemplary nozzle fill method for manufacturing a multi-composition stick product in accordance with the present invention. In FIGS. 7a and 7b, a mold shaft 805 is inserted into at least a portion of the container 815 and the first composition is dispensed either directly or indirectly, for example, using a filling nozzle 820, into the container 815 and around the mold shaft 805. The mold shaft 805 may be solid or have a closed end. After the first composition has cooled and solidified, the mold shaft 805 is removed from the container 815, thereby forming a cavity 825, as shown in FIG. 7c. In FIG. 7d, a second composition is then dispensed into the cavity 825.

Figure 8:
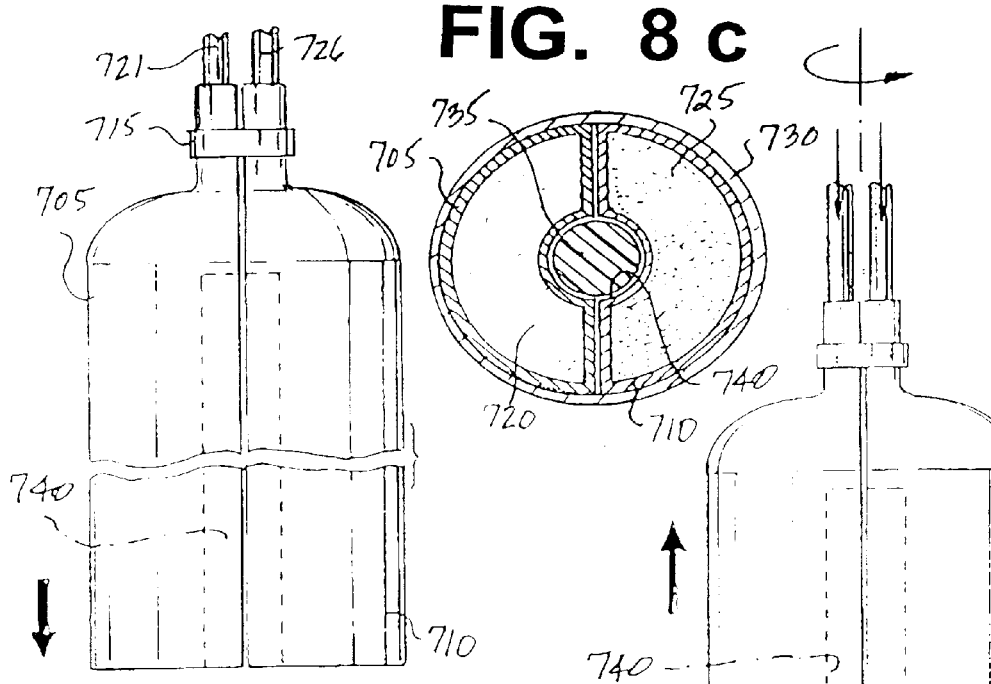
Figure 8:
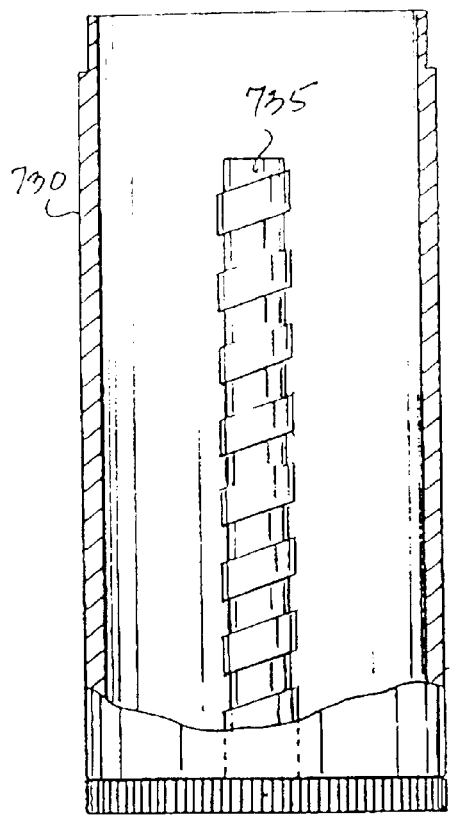
Figure 8:
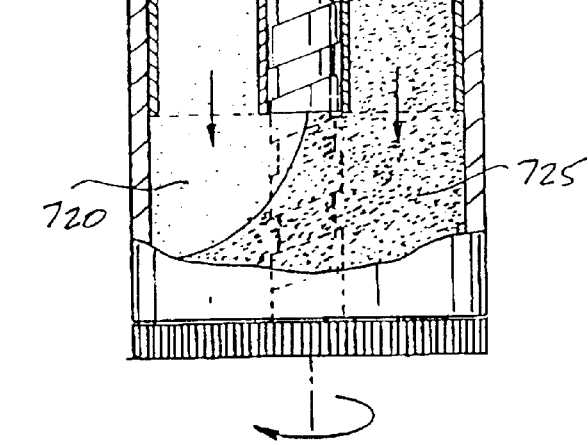

A multi-nozzle system for simultaneously dispensing two or more compositions into a container may be used to create desired patterns in accordance with the present invention. Preferably, each nozzle dispenses a composition at a temperature just above melting temperature. An exemplary dual-nozzle system is shown in FIGS. 8a and 8b. The system includes a first nozzle 705 and a second nozzle 710 connected together by a securing mechanism 715, such as a releaseable ring. The first nozzle 705 has an inlet 721 for receiving a first composition 720 in a liquid state, while the second nozzle 710 receives a second composition 725 in a liquid state through a second inlet 726. In operation the nozzles are assembled together by placing the securing mechanism around both devices, and the assembly is then inserted into the container 730, as shown in FIG. 8a, so that the container screw 735 is received in the recess 740 (FIG. 8c). The first and second compositions 720, 725 are simultaneously dispensed through their respective inlets 721, 726 and nozzles 705, 710 into the container 730 as the assembly is being withdrawn from the container, as shown in FIG. 8b. If the assembly and container are kept stationary, the pattern created is a semicircle. However, if either the assembly or container is rotated with respect to the other, then the design created is that of a spiral shape with intermixing between the colors at the interface between the two compositions. Although this multi-nozzle system has been shown using two nozzles, any number of two or more nozzles may be used. A variety of designs may be produced, such as a circle divided into an even number of wedges, a pinwheel, or a spiral, depending on such factors as the number and shape of the nozzles selected, whether the nozzle or container is rotated with respect to the other, and the angle or degree of rotation. Because the two compositions are dispensed from the mold shafts simultaneously, intermixing between the two compositions will occur at the interface between the two compositions.

Figure 9:
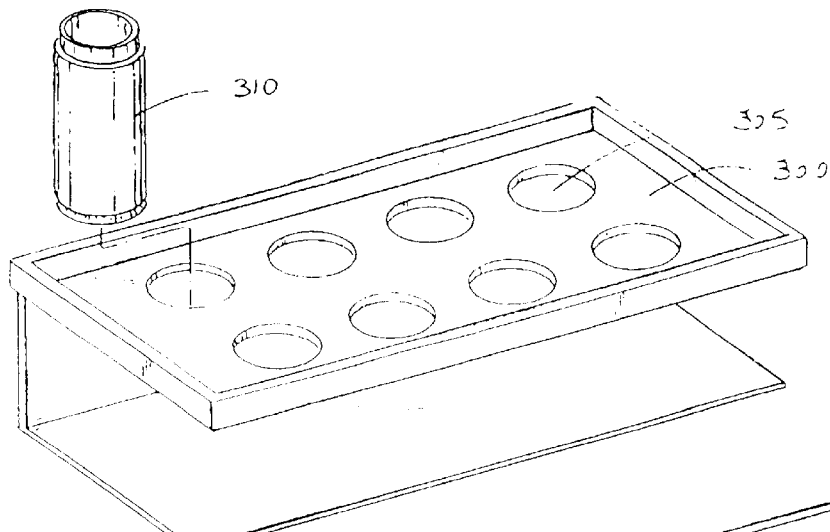
FIGS. 9a–9f show the operating steps of an exemplary flood fill system for manufacturing a multi-composition stick product in accordance with the present invention.
Figure 9:
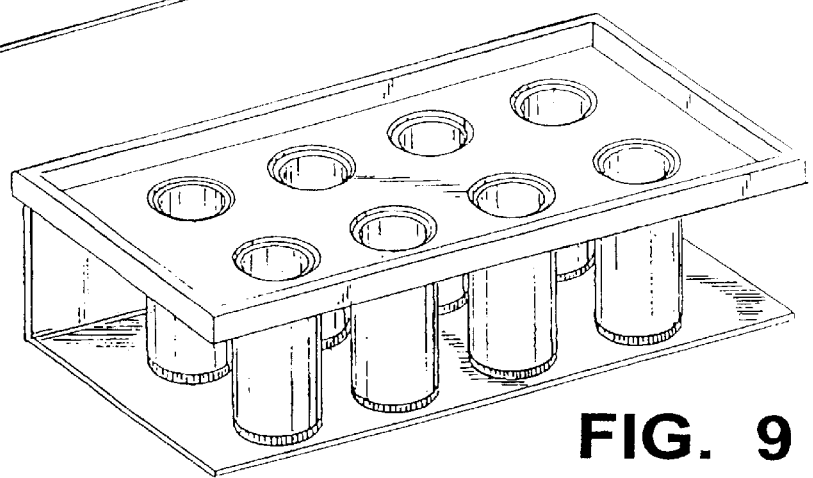
Figure 9:
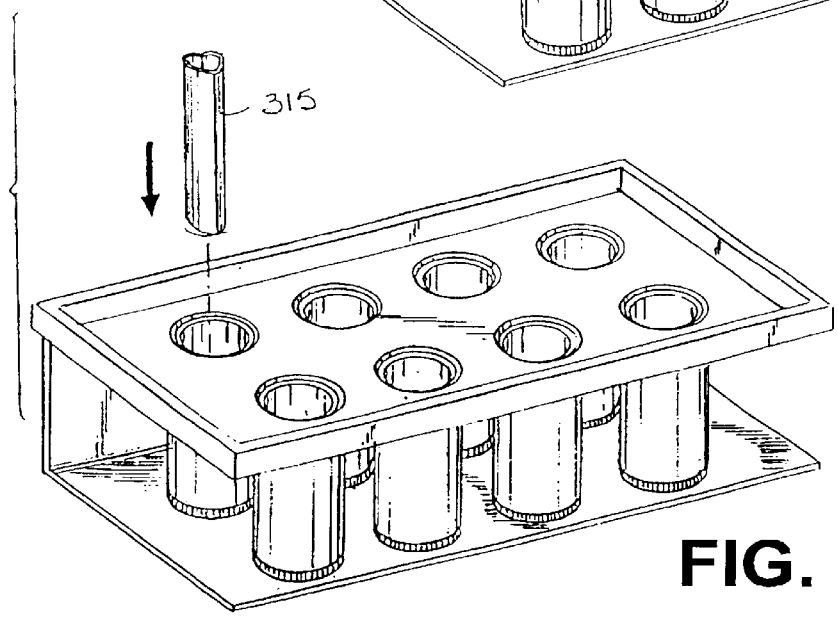
Figure 9:
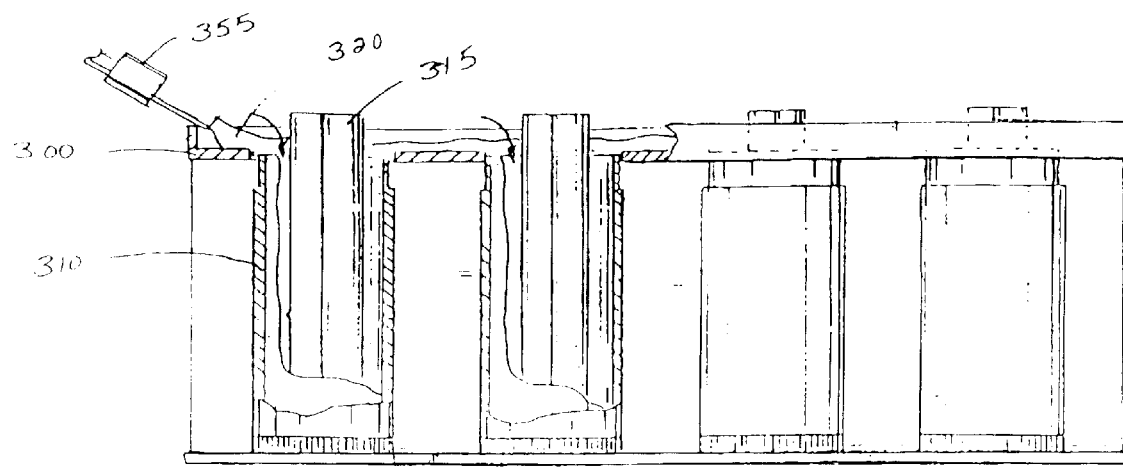
Figure 9:
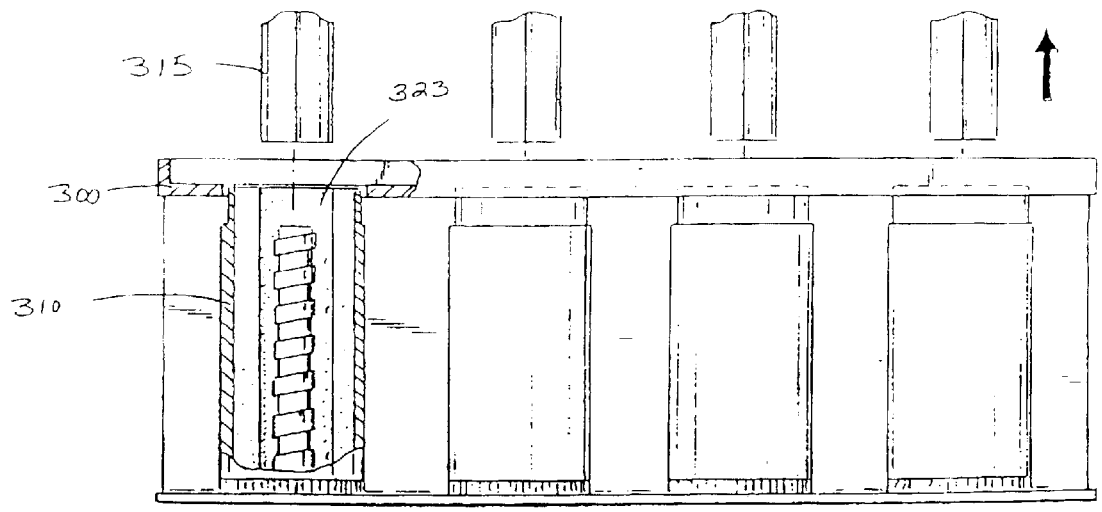
Figure 9:
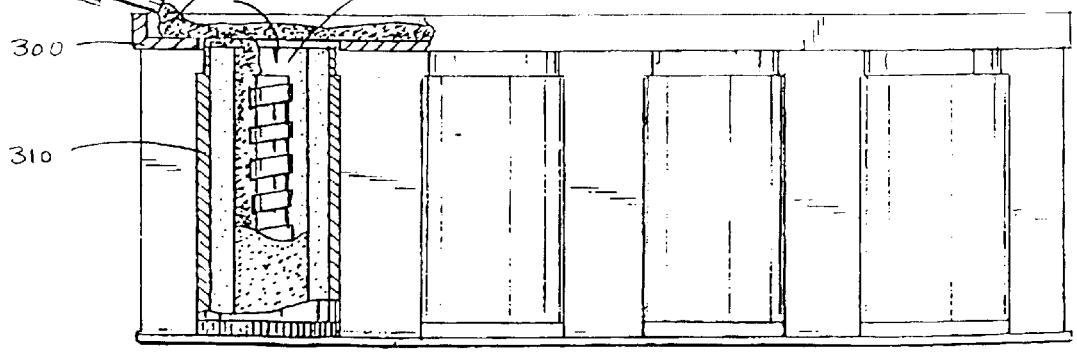

Another embodiment for manufacturing the multi-composition stick product in accordance with the present invention is referred to as the flood fill method. An example flood fill system for simultaneously manufacturing an array or plurality of multi-color stick products is shown in FIGS. 9a–9f. A tray 300 has one or more openings 305 defined therein, each opening is sized to receive a container or housing 310 therein. Although eight openings and associated containers are shown in FIGS. 9a–9f, the system may be modified to accommodate any number of openings and containers, as desired. Typically, an array of 10×20 containers is used. The containers 310 are passed through the openings 305 in the tray 300 until the open end of the container is substantially flush with or recessed relative to the upper surface of the tray. After the containers 310 have been placed in the respective openings 305, a mold shaft 315 is inserted into each of the containers. In FIG. 9d, the mold shaft 315 is inserted so that it contacts the closed end of the container 310 and a portion of the mold shaft projects above the surface of the tray 300. Alternatively, the mold shaft may be inserted into only a portion of the container, e.g. halfway, so that it does not contact the closed end of the container. Mold shaft 315 has any desired shape, such as a heart, as shown. After inserting the mold shaft 315 into the container a valve 335 is opened, as shown in FIG. 9d, and a first composition 320 in a liquid state is poured onto the tray 300, whereby the liquid spills into and fills the container around the mold shaft 315. Once the inner composition cools and solidifies the mold shaft 315 is removed from the container 310 thereby forming a cavity 323 complementary in shape to that of the mold shaft, as shown in FIG. 9e. A second valve 325 is then opened to dispense a second composition 327 in a liquid state onto the tray 300, whereby the liquid spills into and fills the inner cavity left by the mold shaft 315. The top surface of the stick product may be finished, for example, may be scraped using a heated scraper or glazed, without mixing of the first and second compositions. In a preferred embodiment the excess composition is removed, e.g., scraped, from the support tray 300 after the container has been filled with both the first and second compositions. This is disadvantageous, however, in that the excess scrapings from the support tray may not be recycled because the two compositions have formed a mixture. Alternatively, the excess composition may be scraped from the surface of the support tray after the first composition has been dispensed into the container, but before the second composition is dispensed into the container. This alternatively embodiment has the drawback that the scrapings of the first composition may inadvertently be thrown into the cavity form in the container by the first composition. Mold shaft 315 preferably has a relatively small hole defined longitudinally therethrough to relieve air pressure by allowing the air to escape through the hole. thereby making removal of the mold shaft easier. A valve disposed at the top of the hole is closed during filling and opened when the mold shaft is removed from the container.

The flood fill system shown in FIGS. 9a–9f may be modified so as to simultaneously manufacture a plurality of multi-composition stick products. A plurality or array of mold shafts 315 are arranged on a support, similar to the holding member 510 shown in FIG. 5, with each mold shaft disposed substantially centered above an associated stick composition container 310. For example, an array of mold shafts can be arranged for insertion into lip balm containers. All of the mold shafts in the array can be of the same shape. In another embodiment, mold shafts in a given row or column of the array may have the same shape as one another but differ from row to row or column to column. Still another embodiment may have the mold shafts randomly distributed so that each mold shaft is different from all others. Alternatively, the first composition may be dispensed into the container and then the mold shaft may be inserted therein while in a liquid state. Once the first composition has cooled and solidified, the mold shaft is removed to leave or form a cavity that can later be filled with a second composition.

In the fill systems described above, the mold shaft 115, 315 is preferably designed to receive the container screw or shaft 105, if present. Also, the mold shaft 115, 315 is preferably tapered, e.g., about 0.1°, with the wider end disposed towards the open end of the container. The taper facilitates removal of the mold shaft after dispensing the first composition by breaking any vacuum as soon as the mold shaft is removed. Tapering is also advantageous in the nozzle apparatus.

The nozzle fill methods provide better control in filling the container than the flood fill methods.

A multi-composition stick product in accordance with the present invention may be manufactured using a combination of the nozzle fill and flood fill techniques. For example, the container may be filled with the first composition using the nozzle fill technique, and then the second composition may be dispensed into the container using the flood fill technique, or vice versa. It should also be noted that the different compositions may be arranged to form more than one predetermined image in a longitudinal direction of the multi-composition stick product. For instance, the container may be filled with a stick composition in which a first multi-color image in the lower half of the container is a heart surrounded by a circle, while a second multi-color image in the upper half of the container is a broken heart surrounded by a circle. The methods of manufacture described above may be performed while the container is oriented in a vertical direction or may be tilted at a predetermined angle. For example, diagonal stripes may be formed by tilting the angle of orientation of the container.

Figure 10:
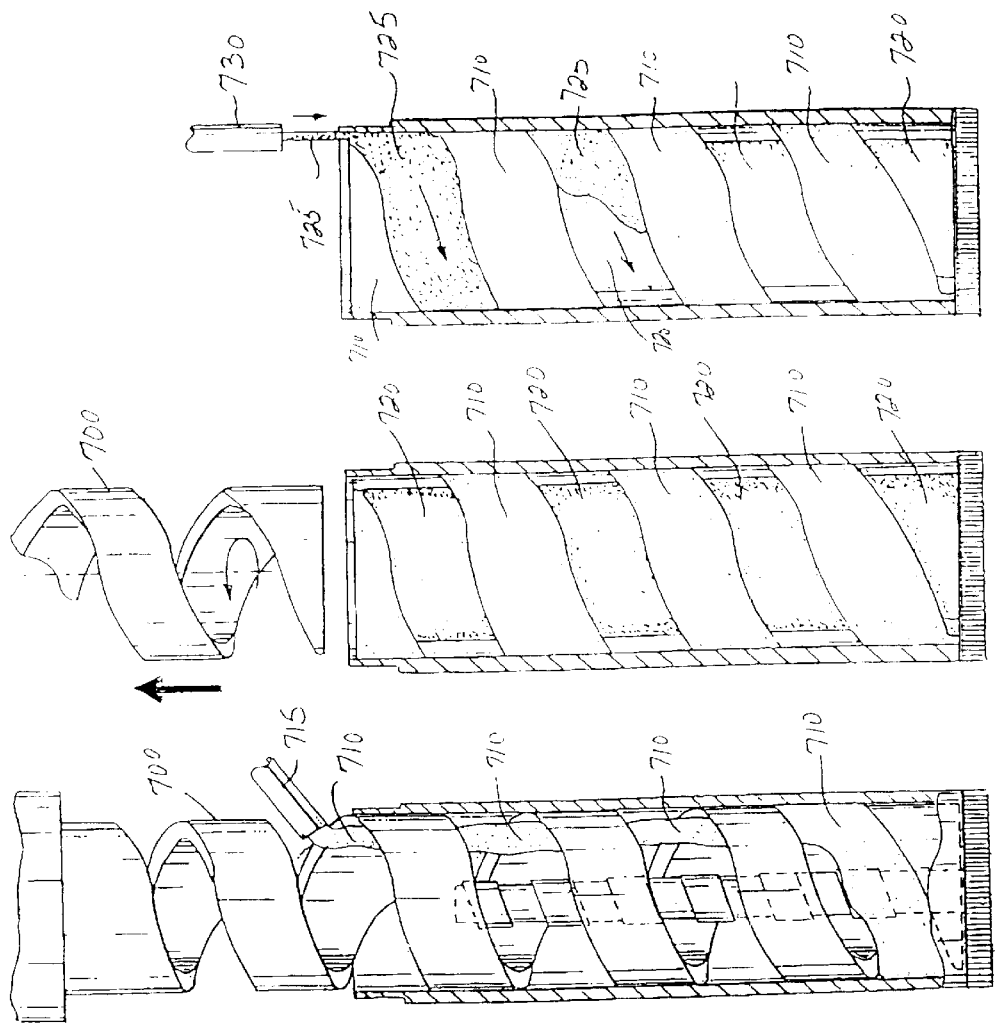
FIGS. 10a–10d show the operating steps of an exemplary cork screw construction of a mold or mold shaft for manufacturing a multi-composition stick product in accordance with the present invention.
Figure 10:
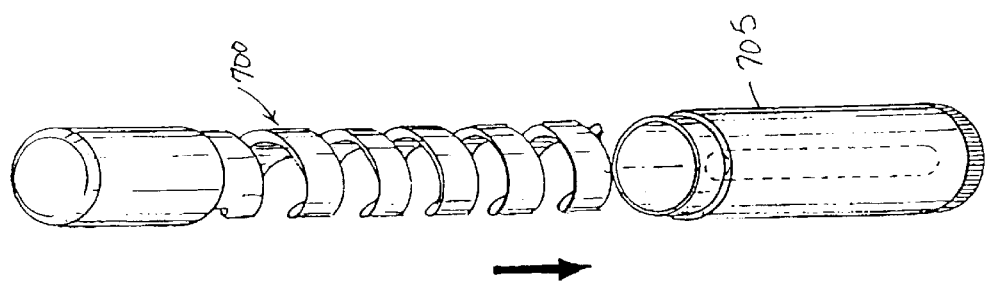

To achieve a multi-composition stick product having a barber pole striped appearance, a mold shaft 700 in the shape of a cork screw may be used, such as that shown in FIGS. 10a–10d. In FIG. 10a, the cork screw shaped mold shaft 700 is inserted into so that it contacts the closed end of the container 705. Alternatively, mold shaft 700 may be inserted partially, e.g. halfway, into the container 705. In FIG. 10b, a first composition 710 in a liquid state is dispensed through a first filling nozzle 715 into the container. After the first composition 710 has cooled and solidified, the mold shaft 700 is rotated in a counter-clockwise direction and extracted from the container without removing or disturbing the first composition thereby leaving cavities 720, as shown in FIG. 10c. Thereafter, in FIG. 10d, the container is then filled with a second composition 725 dispensed from a second filling nozzle 730, using either the nozzle fill or flood fill technique described above, and into the cavities 720. The realized pattern is that of a barber pole.

Referring now to FIGS. 11–19, another embodiment for manufacturing the multi-composition stick product in accordance with the present invention is illustrated. This embodiment is directed to an assembly 900 for mass producing the multi-composition stick products. This assembly 900 includes a conveyor belt 902 that moves a plurality of trays 904 past various stations to produce the multi-composition stick products. A tray 904 has one or more openings 906 defined therein. Each opening is sized to receive a container or housing 908 therein. Although sixty-four openings and associated containers are shown in FIGS. 11–19, the assembly may be modified to accommodate any number of openings and containers, as desired. Typically, an array of 4×16 containers is used. The containers 908 are passed through the openings 906 in the tray 904 until the open end of the container is substantially flush with or recessed relative to the upper surface of the tray. After the containers 908 have been placed in the respective openings 906, an operator will load the tray 904 onto the conveyor belt 902 at one end 910 of the conveyor belt, hereafter referred to as the initial or first end 910. Of course, if desired, the placing of the trays 904 onto belt 902 at first end 910 can be achieved with automated machinery.

Figure 12:
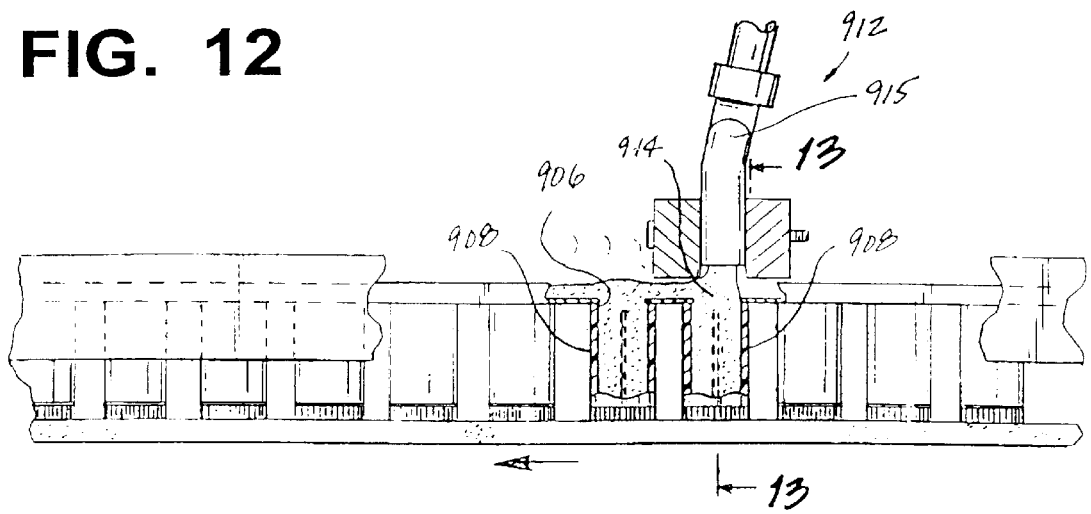
FIG. 12 is a partial side view with parts broken away showing a filling nozzle at a first station of the assembly line illustrated in FIG. 11.
Figure 13:
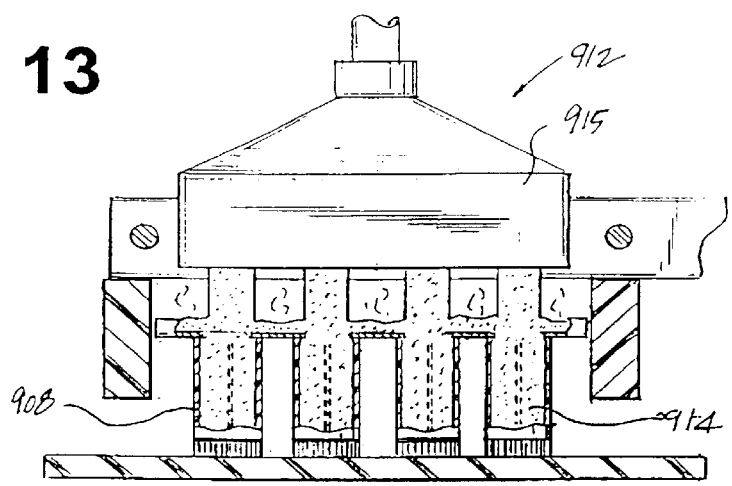
FIG. 13 is a cross-sectional view taken along lines 13—13 of FIG. 12 and looking in the direction of the arrows.

Trays 904 now move on conveyor belt 902 at a predetermined speed, which is about 5.7 feet per minute, to first station 912 to fill each container with a first composition 914, in a liquid state (see FIGS. 12 and 13). Each container 908 must be filled by a predetermined minimal amount or the final product will be rejected for containing insufficient product. Additionally, it is desirable not to overfill each container 908 because excessive waste causes difficulty in downstream stations when extracting or scrapping the excess first composition from the tray 904. One skilled in the art can readily determine the amount of first composition to add at first station 912 to satisfy these criteria. To achieve a precise control of the amount of first composition 914 added at first station 912, a nozzle 915 has a number of ejecting heads equal to the number of containers contained in a row of the tray (e.g., four). Nozzle 915 has an inlet 916 that is fluidly connected to a first composition 914 in a liquid state. Nozzle 915 dispenses the first composition 914 at a temperature of about 160° F., which is about 25° F. above its melting temperature. Thus, immature solidification of the first composition is avoided during a downstream mold insertion stage, to be discussed below. Nozzle 915 has a fan shape to ensure that four uniform streams of liquid are ejected from each head. Each head is preferably disposed essentially above a container 908 as the tray passes below nozzle 915. Typically, a tray 904 will have its first three and last three rows of containers completely filled, and the remaining middle rows are filled about 70–80% by volume. With this nozzle, the tray is filled with about 20–40% excess first composition.

Figure 14:
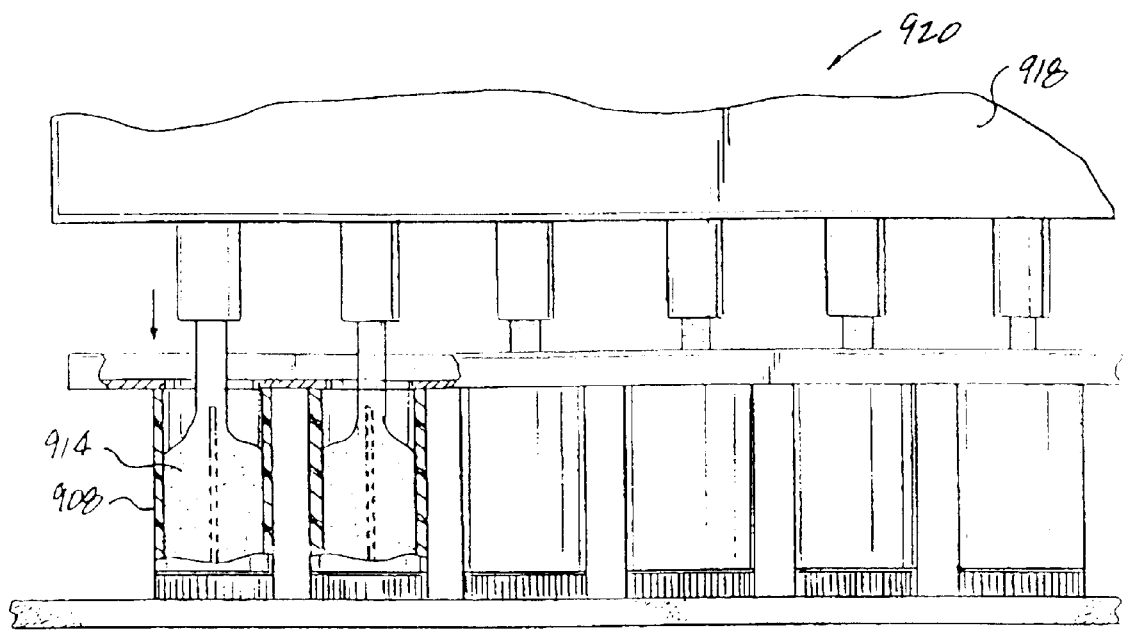
FIG. 14 is a partial side view with parts broken away of another embodiment of filling nozzle.

To achieve a further reduction in the amount of excess first composition, a direct filling nozzle 918 may be use, as shown in FIG. 14. For a 4×16 tray, a 4×16 nozzle assembly 918 will be utilized. In other words, nozzle 918 has sixty-four fluid ejection heads, one for each container. The tray 904 can move continuously or via a stop-and-go movement to fill each individual container 908 of tray 904. Because an individual ejection head injects the first composition directly into only one container per tray, a more precise filling of the container can be achieved. Thus, the tray is filled with significantly less excess first composition.

Figure 15:
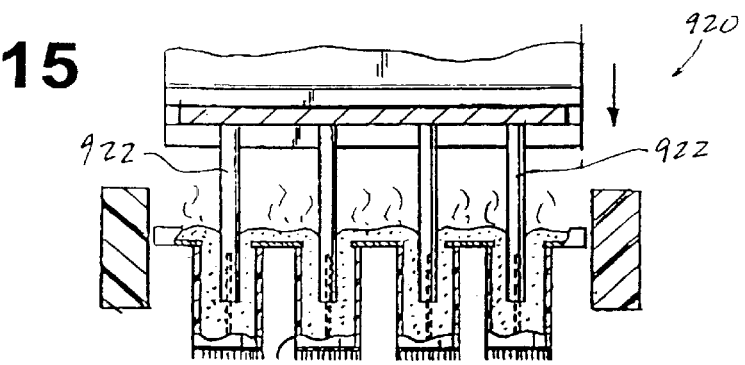
FIG. 15 is a cross-sectional view of a plurality of mold shafts being inserted into containers at a second station of the assembly line.
Figure 16:
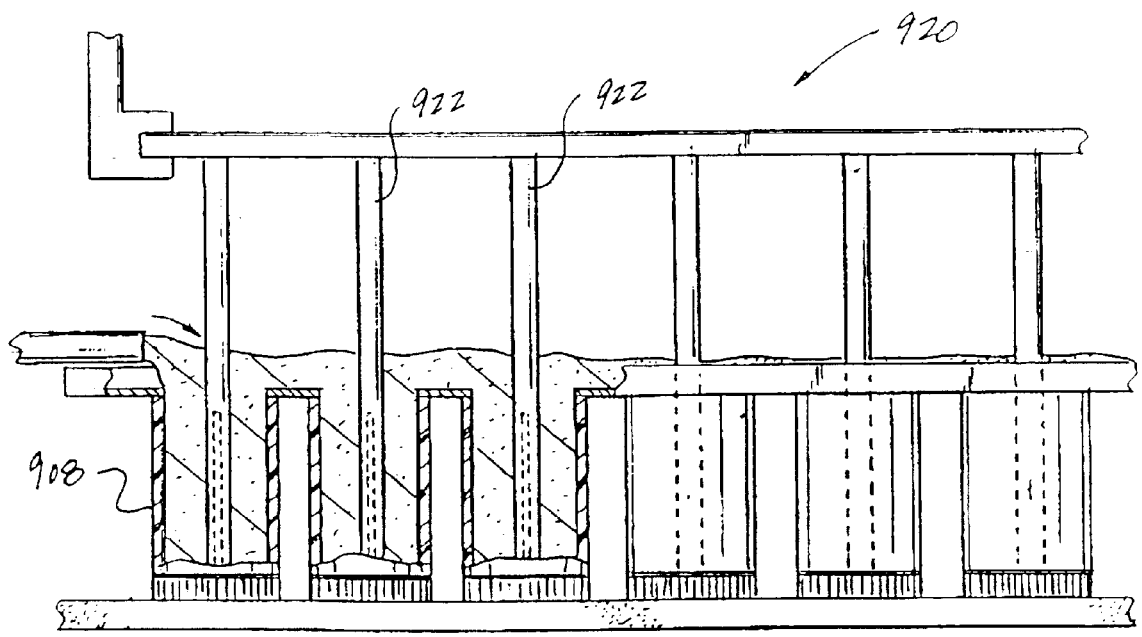
FIG. 16 is a side view with parts broken away of the second station, shown with the mold shafts fully inserted into each container.
Figure 17:
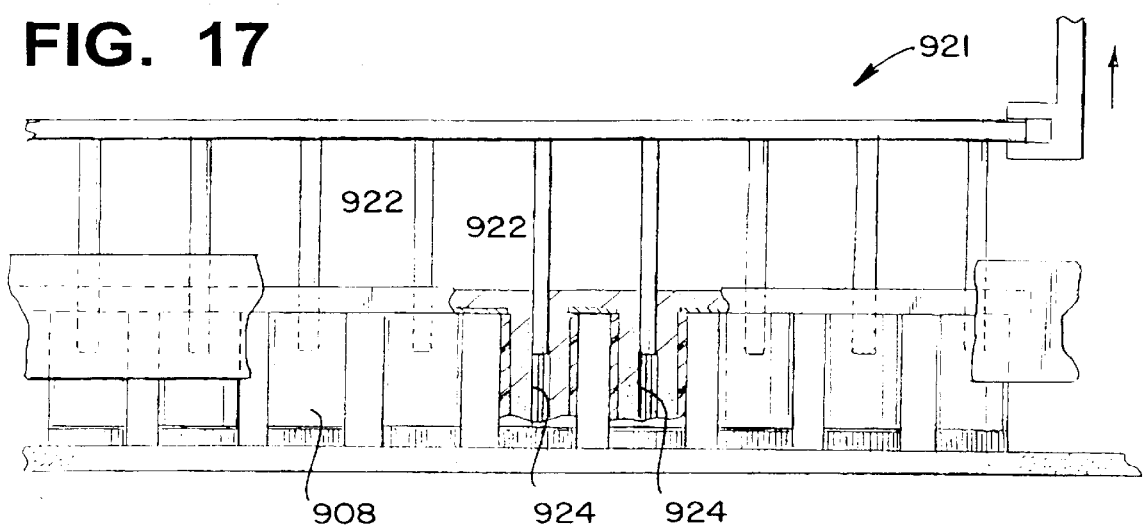
FIG. 17 is a partial side view with parts broken away of a mold shaft being removed from the containers at a third station of the assembly illustrated in FIG. 11.

The tray now filled with a sufficient amount of the first composition travels atop the conveyor belt 902 to a second station 920 so that a mold shaft 922 can be inserted into each container 908 (see FIGS. 15–17). The mold shafts 922 (sixty-four in the exemplary embodiment) are inserted so that they contact the closed end of the container 908 and a portion of the mold shafts project above the surface of the tray 904 (see FIG. 16). Alternatively, the mold shafts 922 may be inserted into only a portion of the container, e.g. halfway, three-fourths, ninety percent of the way down, etc., so that they do not contact the closed end of the container. Mold shafts 922 have any desired shape, such as a heart, star, tree, sun, yin-yang, smiling face, etc. If desired, certain of the mold shafts may have one shape, such as a heart, while others may have a different shape, such as a star.

Second station 920 is disposed downstream from first station 912 by a sufficient distance to ensure that the first composition will still be in a liquid state before the mold shafts are inserted into the containers. Typically, the mold shafts are inserted into the containers within ten seconds after being filled with the first composition. Thus, any air bubbles generated in the containers due to the insertion of the mold shafts easily escape from the containers and the first composition contained within the containers.

Once the first composition cools and solidifies, mold shafts 922 are removed from the container 908, thereby forming a plurality of cavities 924 complementary in shape to that of the respective mold shaft, as shown in FIG. 17. The mold extraction step takes place at third station 921 after the trays 904 have passed through a first cooling tunnel 923.

The mold extraction has to be clean so that the cavity 924 is precisely created after the extraction of the mold shaft from the container. If the first composition over cools, some the first composition will stick to the mold shafts. If the first composition is under cooled, the cavity 924 may collapse during the mold shaft extraction step. It is preferred that the cooling time for the first composition be about two to three minutes at room temperature. It is also preferred that the mold shafts be tapered about at least 0.5 degrees to prevent excessive vacuum build up that may cause the cavity to collapse, as discussed above. Tapers of 1.0 degrees are currently preferred because they effectively prevent vacuum build up, and is also acceptable from an appearance point of view, because such a small taper will appear as 0° in the final product to the average consumer.

It is further preferred that the mold shafts be warmed to about 90–110° F., before the insertion step so that the first composition will not stick to the mold shafts.

The mold shafts preferably have an inner diameter of 3.0 to 3.5 mm to receive the container screw and to produce a more centered inner core shape. The mold shafts also preferably have a beveled opening to permit easy insertion of the shafts into the containers (as shown in FIG. 3b).

The mold shafts are preferably made of a plastic material with a hydrophilic coating, such as, for example, polyester. A TEFLON® coated surface is not preferred because it has been found to create too much adhesion of the first composition onto the mold shafts.

The steps of mold insertion and removal can be done on a continuously moving conveyor belt as illustrated, or on one that stops-and-goes at each station. A stop-and-go production system will produce a more precisely centered pattern, but is more costly and cumbersome to operate. Also, the steps of mold insertion and removal can be achieved at one station.

Figure 11:
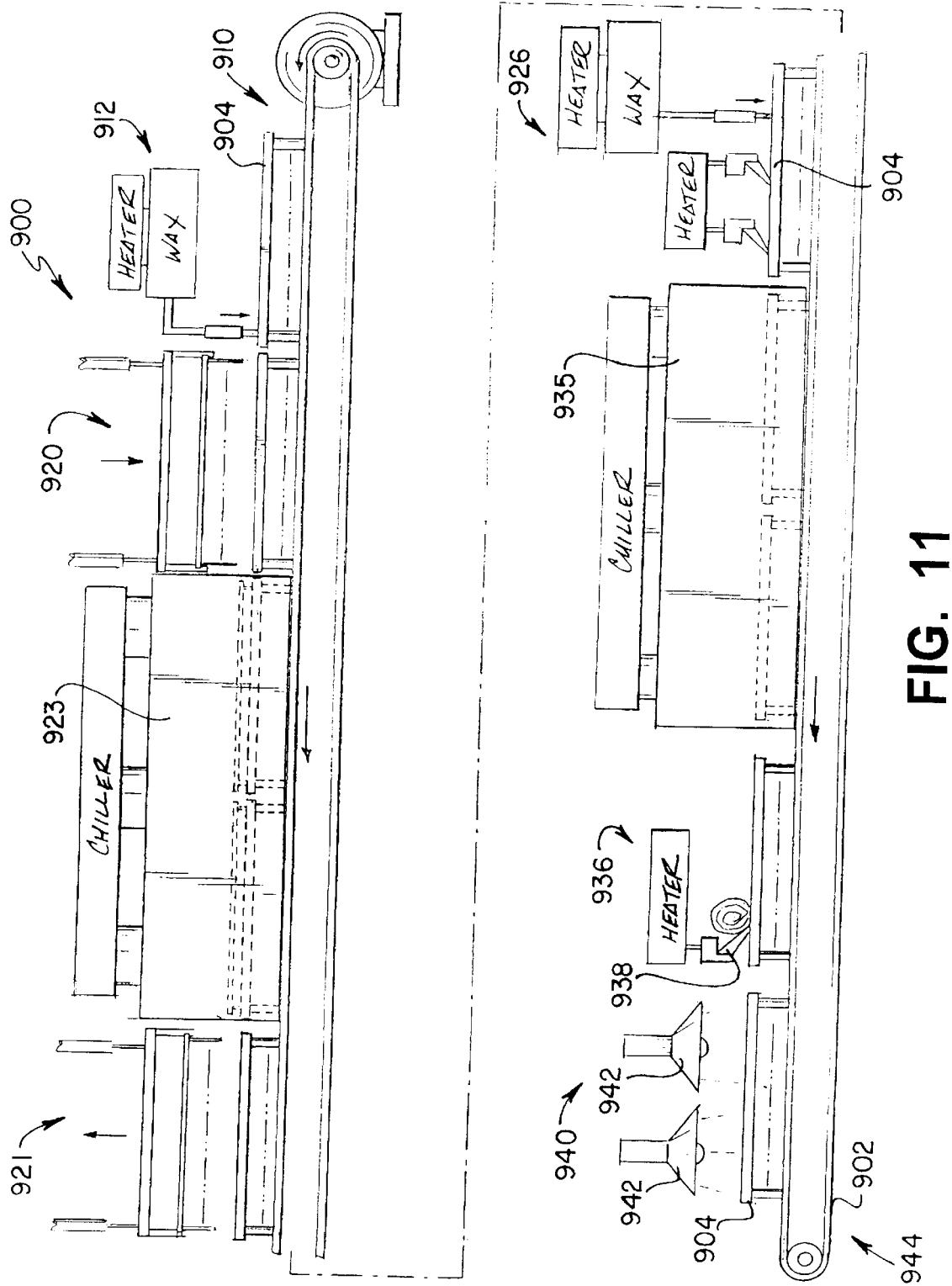
FIG. 11 is a schematic view of another embodiment manufacturing the multi-composition stick product in accordance with the present invention.
Figure 18:
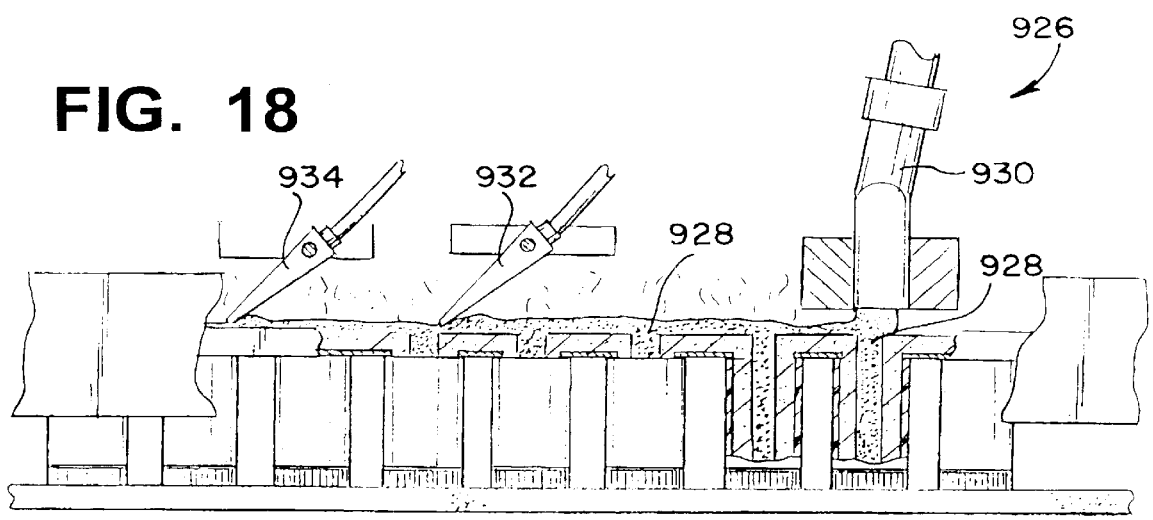
FIG. 18 is a partial side view with parts broken away of a filling nozzle for filling the cavities formed in the first composition in each container with a second composition.

After the mold shafts have been removed from the trays at third station 921, the trays 904 move to a fourth station 926 for filling the trays with a second composition 928, in a liquid state (see FIGS. 11 and 18). Fourth station 926 includes a second nozzle 930 for dispensing a second composition 928 in a liquid state onto tray 904, whereby the liquid spills into and fills the inner cavity 924 left by the mold shafts 922. A first heated metal scraper 932 trails second nozzle 930 by approximately six inches to ensure the excess product completely fills the cavities 924 by pushing the second composition forward toward the cavities. Scraper 932 is preferably set at 150–170° F. The use of scraper 932 causes the amount of second composition excess to be less than 10%. Without the use of scraper 932, second composition excess approaches the 100% level. A high level of excess second composition creates problems when scraping off the excess product, and may lead to a blurred border between the first and second compositions.

Fourth station 926 includes a second heated metal scraper 934 that trails the first scraper 932. Second heated scraper is used to clean the top of the tray. Nozzle 930, first scraper 932, and second scraper 934 are all preferably mounted stationary at station 926, and trays 904 traveling atop conveyor belt 902 moves past each of these structures.

Figure 19:
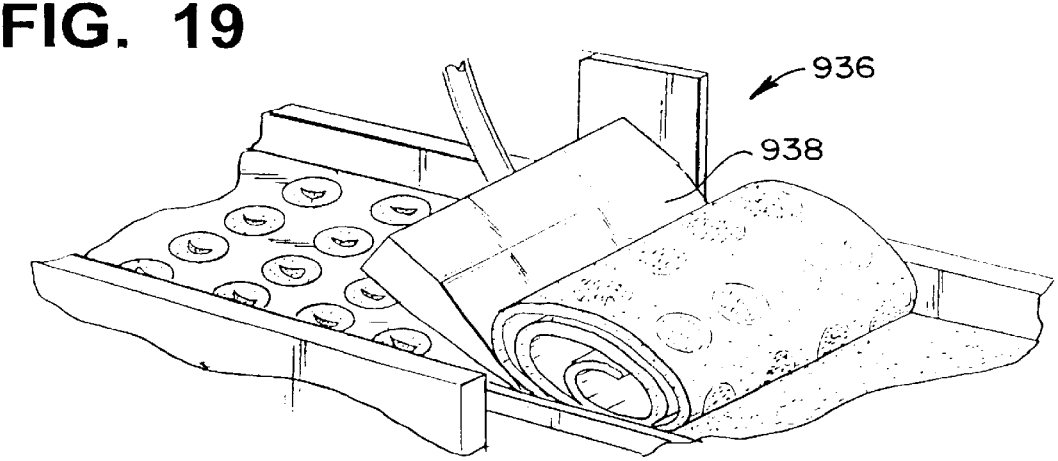
FIG. 19 is a partial perspective view of a scraper to remove excess second composition at a fifth station of the assembly line illustrated in FIG. 11.

The trays 904 are now conveyed to a fifth station 936 where excess second composition is removed from the filled containers 908, by scrapping, and the surface of the scraped filled containers 908 are glazed (see FIGS. 11 and 19). The top surface of the stick product is preferably scrapped with a heated scraper 938, without mixing of the first and second compositions. In a preferred embodiment, the excess composition is removed, e.g., scraped, from the support tray 300 by scraper 938 after the container has been filled with both the first and second compositions. The removal of the composition by scraper 938 preferably takes place about one to two minutes after the trays have been filled with the second composition at fourth station 926. Trays 904 travel through a second cooling tunnel 935 between fourth station 926 and fifth station 936. The time delay must not be too long, or the composition will cool to the point that cracks will occur during or after the scraping with scraper 938. If the time delay is too soon, the composition will not cool enough and the excess will not scrape cleanly from the tray. Scraper 938 is preferably heated between 70° to 300° C., more preferably between 100° to 200° C., and typically about 150°. Scraper 938 also performs a glazing function to the top surface of the first and second compositions. If a sufficient smooth finished surface results, no further glazing will be required.

Should further glazing be required, after the scraping of the excess composition by scraper 938, tray 904 can be glazed by an operator or by automated means with another glazing plate (not shown) to achieve a glazed product for esthetic purposes. The temperature of the glazing plate is preferably set about 70° to 300° C., and more preferably between 100° to 200° C., and typically 150° C. The glazing plate typically contacts the product in one container for less than a second. After glazing, the surface of the product re-solidifies to provide a smooth finished surface.

The scraped tray exiting fifth station 936, may alternatively be glazed at a sixth station 940 by glazing lamps 942 as currently used for conventional single composition lip balm products. The power, timing and position of the glazing lamps can be determined by a person skilled in the art to ensure that a smooth finish is achieved while still maintaining a clear mark of demarcation between the first composition and the second composition.

The trays can now be removed from conveyor belt 902 at its packaging or second end 944. An operator can remove the trays 904 from convey belt 902, so that the containers 908 can be packaged in a conventional manner. Of course, if desired, the removing of trays 904 cam be achieved with automated machinery.

While stick products having two compositions are shown and described, it is within the intended scope of this invention for the stick product to include more than two compositions.

Thus, while there have been shown, described, and pointed out fundamental novel features of the invention as applied to a preferred embodiment thereof, it will be understood that various omissions, substitutions, and changes in the form and details of the devices illustrated, and in their operation, may be made by those skilled in the art without departing from the spirit and scope of the invention. For example, it is expressly intended that all combinations of those elements and/or steps which perform substantially the same function, in substantially the same way, to achieve the same results are within the scope of the invention. Substitutions of elements from one described embodiment to another are also fully intended and contemplated. It is also to be understood that the drawings are not necessarily drawn to scale, but that they are merely conceptual in nature. It is the intention, therefore, to be limited only as indicated by the scope of the claims appended hereto. All patents, patent applications, procedures, and publications cited throughout this application are hereby incorporated by reference in their entireties.

What is claimed is:

1. A method for manufacturing a multi-composition stick product advanceable from an open end of a container, the method comprising the steps of:

inserting a mold shaft into the container;

dispensing a first composition of stick composition into the container around the mold shaft;

removing the mold shaft from the container to form a cavity; and filling at least a portion of the cavity with a second composition of stick composition, the first and second compositions differing by at least one component and being arranged in a predetermined non-random pattern that is reproducible;

wherein the inserting step comprises inserting a portion of a first filling nozzle into the container, the first filling nozzle includes the mold shaft having a first predetermined shape and a first outer barrier disposed about at least a portion of the mold shaft; and wherein the dispensing step comprises dispensing the first composition of stick composition into a passageway, defined between an outer surface of the mold shaft and an inner surface of the first outer barrier, and into the container around the mold shaft.

2. The method in accordance with claim 1, wherein the mold shaft is hollow.

3. The method in accordance with claim 2, wherein the filling step comprises dispensing the second composition of stick composition through the mold shaft and into the container so as to fill at least a portion of the cavity.

4. The method in accordance with claim 1, wherein the first mold shaft is solid or semi-hollow.

5. The method in accordance with claim 4, wherein the filling step comprises dispensing, using a second filling nozzle having a second hollow mold shaft of a second predetermined shape, the second composition of stick composition into the second mold shaft so as to fill at least a portion of the cavity.

6. The method in accordance with claim 1, wherein the dispensing step comprises dispensing the first composition of stick composition into the container around the mold shaft.

7. The method in accordance with claim 1, further comprising the step of finishing a top surface of the stick composition while disposed in the container.

8. The method in accordance with claim 7, wherein said finishing step comprises scraping the top surface of the stick composition with a heated scraper.

9. The method in accordance with claim 7, wherein said finishing step comprises glazing the top surface of the stick composition.

10. The method in accordance with claim 1, wherein the component is a medicament, colorant, fragrance, flavorant, sunscreen, preservative, conditioner, moisturizer, emollient, or surfactant.

11. The method in accordance with claim 10, wherein the component is a colorant.

12. The method in accordance with claim 11, wherein the first and second compositions are arranged as a discrete predetermined non-random multi-color image that is reproducible.

13. The method in accordance with claim 12, wherein for at least a portion of the composition stick, each cross-section in a direction perpendicular to the longitudinal direction of the composition stick has the same image.

14. The method in accordance with claim 1, wherein substantially no mixing occurs at the interface between the first and second compositions.

15. The method in accordance with claim 1, wherein the stick product is a lip balm.

16. The method in accordance with claim 1, wherein the dispensing step comprises dispensing the first composition of stick composition onto a support tray by which the container is held so that the first composition spills into the container around the mold shaft.

17. The method in accordance with claim 16, wherein the filling step comprises dispensing the second composition of stick composition onto the support tray so that the second composition spills into the container and fills at least a portion of the cavity.

18. The method in accordance with claim 17, wherein the removing step further comprises finishing the top surface of the first composition.

19. The method in accordance with claim 1, further comprising the step of removing excess first and second compositions from the support tray.

* * * * *